(12) United States Patent
Stafford

(10) Patent No.: US 11,160,475 B2
(45) Date of Patent: Nov. 2, 2021

(54) SENSOR INSERTER HAVING INTRODUCER

(71) Applicant: ABBOTT DIABETES CARE INC., Alameda, CA (US)

(72) Inventor: Gary Ashley Stafford, Hayward, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 192 days.

(21) Appl. No.: 16/263,155

(22) Filed: Jan. 31, 2019

(65) Prior Publication Data

US 2019/0365297 A1 Dec. 5, 2019

Related U.S. Application Data

(63) Continuation of application No. 14/040,674, filed on Sep. 28, 2013, now Pat. No. 10,226,207, which is a
(Continued)

(51) Int. Cl.
| | |
|---|---|
| A61B 5/1473 | (2006.01) |
| A61B 5/145 | (2006.01) |
| A61B 5/00 | (2006.01) |

(52) U.S. Cl.
CPC ........ *A61B 5/1473* (2013.01); *A61B 5/14532* (2013.01); *A61B 5/14546* (2013.01); *A61B 5/6832* (2013.01)

(58) Field of Classification Search
CPC ............ A61B 5/14503; A61B 5/14532; A61B 5/14546; A61B 5/14552; A61B 5/1473;
(Continued)

(56) References Cited

U.S. PATENT DOCUMENTS

| | | | |
|---|---|---|---|
| 3,123,790 | A | 3/1964 | Tyler |
| 3,211,001 | A | 10/1965 | Petit |
| | | (Continued) | |

FOREIGN PATENT DOCUMENTS

| | | |
|---|---|---|
| DE | 4401400 | 7/1995 |
| EP | 0098592 | 1/1984 |
| | (Continued) | |

OTHER PUBLICATIONS

Alcock, S. J., et al., "Continuous Analyte Monitoring to Aid Clinical Practice", IEEE Engineering in Medicine and Biology Magazine, 1994, pp. 319-325.
(Continued)

*Primary Examiner* — Thomas McEvoy
(74) *Attorney, Agent, or Firm* — One LLP

(57) ABSTRACT

Methods, device and system for providing a sensor insertion assembly including an inserter housing, an introducer including a body portion having a proximal end and a distal end and a shaft portion comprising a channel and a distal end, the shaft portion extending downwardly from an edge of the body portion, the shaft portion including a holding member disposed along a length of the channel, the holding member configured to substantially releasably retain a sensor, an on-body electronics unit, wherein the introducer is configured for insertion of the sensor through an aperture in the on-body electronics unit prior to insertion through skin and a drive mechanism included in the inserter housing and operatively coupled to the introducer, wherein the drive mechanism drives the introducer and retained sensor through the skin are provided.

37 Claims, 19 Drawing Sheets

Related U.S. Application Data continuation-in-part of application No. 13/970,397, filed on Aug. 19, 2013, now Pat. No. 9,480,421, which is a continuation of application No. 11/240,259, filed on Sep. 30, 2005, now Pat. No. 8,512,243, said application No. 14/040,674 is a continuation-in-part of application No. 13/717,501, filed on Dec. 17, 2012, now Pat. No. 8,862,198, which is a continuation of application No. 11/530,472, filed on Sep. 10, 2006, now Pat. No. 8,333,714, said application No. 14/040,674 is a continuation-in-part of application No. 13/434,804, filed on Mar. 29, 2012, now Pat. No. 9,743,862, and a continuation-in-part of application No. 13/171,401, filed on Jun. 28, 2011, now Pat. No. 9,572,534, and a continuation-in-part of application No. 13/022,616, filed on Feb. 7, 2011, now Pat. No. 10,194,863, which is a continuation of application No. 11/240,257, filed on Sep. 30, 2005, now Pat. No. 7,883,464, said application No. 14/040,674 is a continuation-in-part of application No. 12/895,015, filed on Sep. 30, 2010, now Pat. No. 9,351,669, and a continuation-in-part of application No. 12/893,974, filed on Sep. 29, 2010, now abandoned, and a continuation-in-part of application No. 12/873,302, filed on Aug. 31, 2010, now abandoned, and a continuation-in-part of application No. 12/873,301, filed on Aug. 31, 2010, now abandoned, and a continuation-in-part of application No. 12/870,818, filed on Aug. 28, 2010, now abandoned, and a continuation-in-part of application No. 12/795,634, filed on Jun. 7, 2010, now Pat. No. 8,602,991, which is a continuation of application No. 11/216,932, filed on Aug. 30, 2005, now Pat. No. 7,731,657, said application No. 14/040,674 is a continuation-in-part of application No. 12/571,349, filed on Sep. 30, 2009, now Pat. No. 8,852,101, which is a continuation of application No. 11/535,983, filed on Sep. 28, 2006, now Pat. No. 7,697,967, said application No. 14/040,674 is a continuation-in-part of application No. 12/129,573, filed on May 29, 2008, now Pat. No. 8,613,703, and a continuation-in-part of application No. 12/032,593, filed on Feb. 15, 2008, now Pat. No. 9,636,450, and a continuation-in-part of application No. 11/617,698, filed on Dec. 28, 2006, now Pat. No. 8,545,403, and a continuation-in-part of application No. 11/552,072, filed on Oct. 23, 2006, now Pat. No. 9,788,771, and a continuation-in-part of application No. 11/552,065, filed on Oct. 23, 2006, now Pat. No. 9,259,175, and a continuation-in-part of application No. 11/530,473, filed on Sep. 10, 2006, now Pat. No. 9,398,882, which is a continuation-in-part of application No. 11/240,259, filed on Sep. 30, 2005, now Pat. No. 8,512,243, said application No. 14/040,674 is a continuation-in-part of application No. 11/192,773, filed on Jul. 29, 2005, now abandoned, and a continuation-in-part of application No. 11/027,230, filed on Dec. 29, 2004, now Pat. No. 8,571,624, and a continuation-in-part of application No. 11/026,766, filed on Dec. 29, 2004, now abandoned, and a continuation-in-part of application No. 13/252,118, filed on Oct. 3, 2011, now Pat. No. 9,364,149, which is a continuation of application No. 11/365,334, filed on Feb. 28, 2006, now Pat. No. 8,029,441, said application No. 14/040,674 is a continuation-in-part of application No. 11/380,883, filed on Apr. 28, 2006, now abandoned.

(60) Provisional application No. 61/470,454, filed on Mar. 31, 2011, provisional application No. 61/359,816, filed on Jun. 29, 2010, provisional application No. 61/247,516, filed on Sep. 30, 2009, provisional application No. 61/246,825, filed on Sep. 29, 2009, provisional application No. 61/238,537, filed on Aug. 31, 2009, provisional application No. 61/238,483, filed on Aug. 31, 2009, provisional application No. 61/238,494, filed on Aug. 31, 2009, provisional application No. 61/238,159, filed on Aug. 29, 2009, provisional application No. 60/754,870, filed on Dec. 28, 2005, provisional application No. 60/941,060, filed on May 31, 2007, provisional application No. 60/890,497, filed on Feb. 19, 2007, provisional application No. 60/754,870, filed on Dec. 28, 2005.

(58) Field of Classification Search
CPC ..... A61B 5/6848; A61B 5/6849; A61B 5/685; A61B 5/150358; A61B 5/150511; A61B 5/150419; A61B 5/15045; A61B 5/14528; A61B 5/1459; A61B 5/1464; A61B 5/14865; A61B 5/15; A61B 5/15; A61B 2562/0295; A61B 2562/227; A61B 17/34; A61B 17/3403; A61B 5/15101–15198; A61B 2017/00349; A61B 2017/3409; A61M 25/0643; A61M 25/065; A61M 25/06; A61M 5/14244; A61M 5/14248; A61M 2025/0656

See application file for complete search history.

(56) References Cited

U.S. PATENT DOCUMENTS

| | | |
|---|---|---|
| 3,260,656 A | 7/1966 | Ross, Jr. |
| 3,581,062 A | 5/1971 | Aston |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |

(56) References Cited

U.S. PATENT DOCUMENTS

| | | |
|---|---|---|
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,622,966 A | 11/1986 | Beard |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,683 A | 11/1988 | Wozniak et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Cuny |
| 4,985,142 A * | 1/1991 | Laycock ............. B01D 35/147 210/130 |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,002,054 A | 3/1991 | Ash et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |

(56) References Cited

U.S. PATENT DOCUMENTS

| | | |
|---|---|---|
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,193,545 A | 3/1993 | Marsoner et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,472,317 A | 12/1995 | Field et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,533,977 A | 7/1996 | Matcalf et al. |
| 5,543,326 A | 8/1996 | Heller et al. |
| 5,545,191 A | 8/1996 | Mann et al. |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Amdt et al. |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,071 A | 9/1997 | Wyrick |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,697 A | 5/1998 | Swedlow et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsais et al. |
| 5,865,804 A | 2/1999 | Bachynsky |
| 5,871,494 A | 2/1999 | Simons et al. |
| 5,885,211 A | 3/1999 | Eppstein et al. |
| 5,899,855 A | 5/1999 | Brown |
| 5,918,603 A | 7/1999 | Brown |
| 5,924,979 A | 7/1999 | Sedlow et al. |
| 5,925,021 A | 7/1999 | Castellano et al. |
| 5,931,814 A | 8/1999 | Alex et al. |
| 5,931,868 A | 8/1999 | Gross et al. |
| 5,938,679 A | 8/1999 | Freeman et al. |
| 5,948,006 A | 9/1999 | Mann |
| 5,951,492 A | 9/1999 | Douglas et al. |
| 5,951,521 A | 9/1999 | Mastrototaro et al. |
| 5,951,582 A | 9/1999 | Thome et al. |
| 5,954,643 A | 9/1999 | Van Antwerp |
| 5,954,685 A | 9/1999 | Tierny |

(56) References Cited

U.S. PATENT DOCUMENTS

| | | |
|---|---|---|
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,971,941 A | 10/1999 | Simons et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,036,924 A | 3/2000 | Simons et al. |
| 6,048,352 A | 4/2000 | Douglas et al. |
| 6,049,727 A | 4/2000 | Crothall |
| 6,056,718 A | 5/2000 | Funderburk et al. |
| 6,059,946 A | 5/2000 | Yukawa et al. |
| 6,068,399 A | 5/2000 | Tseng |
| 6,071,294 A | 6/2000 | Simons et al. |
| 6,071,391 A | 6/2000 | Gotoh et al. |
| 6,083,710 A | 7/2000 | Heller et al. |
| 6,088,605 A | 7/2000 | Griffith et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,099,484 A | 8/2000 | Douglas et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,168,606 B1 | 1/2001 | Levin et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,302,866 B1 | 10/2001 | Marggi |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Antwerp et al. |
| 6,368,274 B1 | 4/2002 | Antwerp et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,409,740 B1 | 6/2002 | Kuhr et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,440,068 B1 | 8/2002 | Brown et al. |
| 6,445,374 B2 | 9/2002 | Albert et al. |
| 6,458,109 B1 | 10/2002 | Henley et al. |
| 6,461,496 B1 | 10/2002 | Feldman et al. |
| 6,472,220 B1 | 10/2002 | Simons et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,522,927 B1 | 2/2003 | Bishay et al. |
| 6,540,891 B1 | 4/2003 | Stewart et al. |
| 6,546,268 B1 | 4/2003 | Ishikawa et al. |
| 6,551,494 B1 | 4/2003 | Heller et al. |
| 6,551,496 B1 | 4/2003 | Moles et al. |
| 6,554,795 B2 | 4/2003 | Lam et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,650,471 B2 | 11/2003 | Doi |
| 6,654,625 B1 | 11/2003 | Say et al. |
| 6,659,948 B2 | 12/2003 | Lebel et al. |
| 6,666,849 B1 | 12/2003 | Marshall et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,730,200 B1 | 5/2004 | Stewart et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,758,835 B2 | 7/2004 | Close et al. |
| 6,764,581 B1 | 7/2004 | Forrow et al. |
| 6,770,030 B1 | 8/2004 | Schaupp et al. |

(56) References Cited

U.S. PATENT DOCUMENTS

| | | |
|---|---|---|
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Ughigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,265 B2 | 5/2005 | Silver |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,010,356 B2 | 3/2006 | Jog et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,682,338 B2 | 3/2010 | Griffin |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford. |
| 7,736,344 B2 | 6/2010 | Moberg et al. |
| 7,763,042 B2 | 7/2010 | Iio et al. |
| 7,766,829 B2 | 8/2010 | Sloan et al. |
| 7,822,454 B1 | 10/2010 | Alden et al. |
| 7,866,026 B1 | 1/2011 | Wang et al. |
| 7,883,464 B2 | 2/2011 | Stafford |
| 8,512,243 B2 | 8/2013 | Stafford |
| 2001/0034479 A1 | 10/2001 | Ring et al. |
| 2002/0002344 A1 | 1/2002 | Douglas et al. |
| 2002/0013538 A1 | 1/2002 | Teller |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0050250 A1 | 5/2002 | Peterson et al. |
| 2002/0055711 A1 | 5/2002 | Lavi et al. |
| 2002/0057993 A1 | 5/2002 | Maisey et al. |
| 2002/0066764 A1 | 6/2002 | Perry et al. |
| 2002/0072720 A1 | 6/2002 | Hague et al. |
| 2002/0076966 A1 | 6/2002 | Carron et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0133066 A1 | 9/2002 | Miller et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0165462 A1 | 11/2002 | Westbrook et al. |
| 2002/0169369 A1 | 11/2002 | Ward et al. |
| 2002/0169439 A1 | 11/2002 | Flaherty et al. |
| 2002/0198444 A1 | 12/2002 | Ughigaki et al. |
| 2002/0198543 A1 | 12/2002 | Burdulis et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0055380 A1 | 3/2003 | Flaherty |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |

(56) References Cited

U.S. PATENT DOCUMENTS

| | | |
|---|---|---|
| 2003/0078560 A1 | 4/2003 | Miller et al. |
| 2003/0083686 A1 | 5/2003 | Freeman et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2003/0236489 A1 | 12/2003 | Jacobson et al. |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0006413 A1 | 4/2004 | Miller et al. |
| 2004/0064068 A1 | 4/2004 | DeNuzzio et al. |
| 2004/0072357 A1 | 4/2004 | Steine et al. |
| 2004/0096959 A1 | 5/2004 | Steine et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0122353 A1 | 6/2004 | Shahmirian et al. |
| 2004/0122489 A1 | 6/2004 | Mazar et al. |
| 2004/0133164 A1* | 7/2004 | Funderburk .......... A61B 5/6833 604/134 |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0162521 A1 | 8/2004 | Bengtsson et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0210122 A1 | 10/2004 | Sleburg |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0038465 A1* | 2/2005 | Shraga ............... A61B 5/15113 606/182 |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096520 A1 | 5/2005 | Maekawa et al. |
| 2005/0101912 A1 | 5/2005 | Faust et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0149066 A1 | 7/2005 | Stafford |
| 2005/0154410 A1 | 7/2005 | Conway et al. |
| 2005/0159678 A1 | 7/2005 | Taniike et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0267327 A1 | 12/2005 | Iizuka et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047220 A1 | 3/2006 | Sakata et al. |
| 2006/0091006 A1 | 5/2006 | Wang et al. |
| 2006/0095014 A1 | 5/2006 | Ethelfeld |
| 2006/0129173 A1 | 6/2006 | Wilkinson |
| 2006/0135908 A1 | 6/2006 | Liniger et al. |
| 2006/0155210 A1 | 7/2006 | Beckman et al. |
| 2006/0155317 A1 | 7/2006 | List et al. |
| 2006/0161664 A1 | 7/2006 | Motoyama |
| 2006/0166629 A1 | 7/2006 | Reggiardo |
| 2006/0173444 A1 | 8/2006 | Choy et al. |
| 2006/0181695 A1 | 8/2006 | Sage, Jr. |
| 2006/0183985 A1 | 8/2006 | Brister et al. |
| 2006/0189863 A1 | 8/2006 | Peyser et al. |
| 2006/0189939 A1 | 8/2006 | Gonnelli et al. |
| 2006/0193375 A1 | 8/2006 | Lee |
| 2006/0195029 A1 | 8/2006 | Shults et al. |

(56) References Cited

U.S. PATENT DOCUMENTS

| | | |
|---|---|---|
| 2006/0200181 A1 | 9/2006 | Fukuzawa et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0253086 A1 | 11/2006 | Moberg et al. |
| 2006/0258929 A1 | 11/2006 | Goode, Jr. et al. |
| 2006/0258939 A1 | 11/2006 | Pesach et al. |
| 2006/0258959 A1 | 11/2006 | Sode |
| 2006/0264888 A1 | 11/2006 | Moberg et al. |
| 2006/0276724 A1 | 12/2006 | Freeman et al. |
| 2006/0282042 A1 | 12/2006 | Walters et al. |
| 2006/0287591 A1 | 12/2006 | Ocvirk et al. |
| 2007/0016381 A1 | 1/2007 | Kamath et al. |
| 2007/0027381 A1 | 2/2007 | Stafford |
| 2007/0038044 A1 | 2/2007 | Dobbies et al. |
| 2007/0056858 A1 | 3/2007 | Chen et al. |
| 2007/0060814 A1 | 3/2007 | Stafford |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0088377 A1 | 4/2007 | Levaughn et al. |
| 2007/0093754 A1 | 4/2007 | Mogensen et al. |
| 2007/0010613 A1 | 5/2007 | Sloan et al. |
| 2007/0095661 A1 | 5/2007 | Wang et al. |
| 2007/0108048 A1 | 5/2007 | Wang et al. |
| 2007/0110124 A1 | 5/2007 | Shiraki et al. |
| 2007/0123819 A1 | 5/2007 | Memoe et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0197889 A1 | 8/2007 | Brister et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0219496 A1 | 9/2007 | Kamen et al. |
| 2007/0227911 A1 | 10/2007 | Wang et al. |
| 2007/0232879 A1 | 10/2007 | Brister et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0064944 A1 | 3/2008 | Antwerp et al. |
| 2008/0065646 A1 | 3/2008 | Zhang et al. |
| 2008/0066305 A1 | 3/2008 | Wang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0148873 A1 | 6/2008 | Wang |
| 2008/0167572 A1 | 7/2008 | Stivoric et al. |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214481 A1 | 9/2008 | Challoner et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0255440 A1 | 10/2008 | Eilersen et al. |
| 2008/0262330 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048563 A1 | 2/2009 | Ethelfeld et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |

(56) References Cited

U.S. PATENT DOCUMENTS

| | | |
|---|---|---|
| 2009/0105569 A1 | 4/2009 | Stafford |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Gryn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204653 A1 | 8/2010 | Gryn et al. |
| 2010/0212583 A1 | 8/2010 | Brister et al. |
| 2010/0213057 A1 | 8/2010 | Feldman et al. |
| 2010/0214104 A1 | 8/2010 | Goode et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode et al. |
| 2010/0240976 A1 | 9/2010 | Goode et al. |
| 2010/0261987 A1 | 10/2010 | Kamath et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0326842 A1 | 12/2010 | Mazza et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |

(56) References Cited

U.S. PATENT DOCUMENTS

| | | |
|---|---|---|
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0077659 A1 | 3/2011 | Mandecki et al. |
| 2011/0082484 A1 | 4/2011 | Saravia et al. |
| 2011/0106126 A1 | 5/2011 | Love et al. |
| 2011/0118579 A1 | 5/2011 | Goode et al. |
| 2011/0118580 A1 | 5/2011 | Goode et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gym et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0191044 A1 | 8/2011 | Stafford |
| 2011/0201910 A1 | 8/2011 | Rasdal et al. |
| 2011/0201911 A1 | 8/2011 | Johnson et al. |
| 2011/0213225 A1 | 9/2011 | Bernstein et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0288574 A1 | 11/2011 | Cuny et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0108983 A1 | 5/2012 | Banet et al. |
| 2012/0123385 A1 | 5/2012 | Edwards et al. |
| 2012/0184909 A1 | 7/2012 | Gym et al. |
| 2012/0296327 A1 | 11/2012 | Hutchins et al. |
| 2013/0047981 A1 | 2/2013 | Bacon |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2004-520103 | 7/2004 |
| JP | 2004-520898 | 7/2004 |
| WO | WO-1996/039977 | 5/1996 |
| WO | WO-1996/025089 | 8/1996 |
| WO | WO-1996/035370 | 11/1996 |
| WO | WO-1997/021457 | 6/1997 |
| WO | WO-1998/035053 | 8/1998 |
| WO | WO-1998/056293 | 12/1998 |
| WO | WO-1999/033504 | 7/1999 |
| WO | WO-1999/056613 | 11/1999 |
| WO | WO-2000/049940 | 8/2000 |
| WO | WO-2000/059370 | 10/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/050534 | 6/2002 |
| WO | WO-2002/058537 | 8/2002 |
| WO | WO-2003/028784 | 4/2003 |
| WO | WO-2003/073936 | 9/2003 |
| WO | WO-2003/076893 | 9/2003 |
| WO | WO-2003/082091 | 10/2003 |
| WO | WO-2004/054445 | 7/2004 |
| WO | WO-2004/060436 | 7/2004 |
| WO | WO-2004/061420 | 7/2004 |
| WO | WO-2005/037184 | 4/2005 |
| WO | WO-2005/084534 | 9/2005 |
| WO | WO-2005/089103 | 9/2005 |
| WO | WO-2006/042811 | 4/2006 |
| WO | WO-2006/108809 | 10/2006 |
| WO | WO-2007/097754 | 8/2007 |
| WO | WO-2007/140783 | 12/2007 |
| WO | WO-2008/065646 | 6/2008 |
| WO | WO-2008/133702 | 11/2008 |
| WO | WO-2009/062675 | 5/2009 |
| WO | WO-2010/112521 | 10/2010 |
| WO | WO-2011/002815 | 1/2011 |

OTHER PUBLICATIONS

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1071.

Bennion, N., et al., "Alternate Site Glucose Testing: A Crossover Design", Diabetes Technology & Therapeutics, vol. 4, No. 1, 2002, pp. 25-33.

Bindra, D. S., et al., "Design and in Vitro Studies of a Needle-Type Glucose Sensor for Subcutaneous Monitoring", Analytical Chemistry, vol. 63, No. 17, 1991, pp. 1692-1696.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Bobbioni-Harsch, E., et al., "Lifespan of Subcutaneous Glucose Sensors and Their Performances During Dynamic Glycaemia Changes in Rats", Journal of Biomedical Engineering, vol. 15, 1993, pp. 457-463.

Brooks, S. L., et al., "Development of an On-Line Glucose Sensor for Fermentation Monitoring", Biosensors, vol. 3, 1987/88, pp. 45-56.

Cass, A. E., et al., "Ferrocene-Mediated Enzyme Electrode for Amperometric Determination of Glucose", Analytical Chemistry, vol. 56, No. 4, 1984, 667-671.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

(56) References Cited

OTHER PUBLICATIONS

Dexcom, "STS User's Guide", DexCom, Inc., 2006, pp. 1-111.
Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Gregg, B. A., et al., "Cross-Linked Redox Gels Containing Glucose Oxidase for Amperometric Bionsensor Applications", Analytical Chemistry, vol. 62, No. 3, 1990, pp. 258-263.
Gunasingham, et al., "Electrochemically Modulated Optrode for Glucose", Biosensors & Bioelectronics, vol. 7, 1992, pp. 353-359.
Harrison, D. J., et al., "Characterization of Perfluorosulfonic Acid Polymer Coated Enzyme Electrodes and a Miniatureized Integrated Potentiostat for Glucose Analysis in Whole Blood", Analytical Chemistry, vol. 60, No. 19, 1988, pp. 2002-2007.
Heller, A., "Electrical Connection Enzyme Redox Centers to Electrodes", Journal of Physical Chemistry, vol. 96, No. 9, 1990, pp. 3579-3587.
Ikeda, T., et al., "Artificial Pancreas—Investigation of the Stability of Glucose Sensors Using a Telemetry System" (English language translation of abstract), Jpn. J. Artif. Organs, vol. 19, No. 2, 1990, pp. 889-892.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, K. W., et al., "In vivo Evaluation of an Electroenzymatic Glucose Sensor Implanted in Subcutaneous Tissue", Biosensors & Bioelectronics, vol. 7, 1992, pp. 709-714.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Lortz, J., et al., "What is Bluetooth? We Explain The Newest Short-Range Connectivity Technology", Smart Computing Learning Series, Wireless Computing, vol. 8, Issue 5, 2002, pp. 72-74.
Maidan, R., et al., "Elimination of Electrooxidizable Interferant-Produced Currents in Amperometric Biosensors", Analytical Chemistry, vol. 64, No. 23, 1992, pp. 2889-2896.
Malin, S. F., et al., "Noninvasive Prediction of Glucose by Near-Infrared Diffuse Reflectance Spectroscopy", Clinical Chemistry, vol. 45, No. 9, 1999, pp. 1651-1658.
Mastrototaro, J. J., et al., "An Electroenzymatic Glucose Sensor Fabricated on a Flexible Substrate", Sensors and Actuators B, vol. 5, 1991, pp. 139-144.
Mcgarraugh, G., et al., "Glucose Measurements Using Blood Extracted from the Forearm and the Finger", TheraSense, Inc., 2001, 16 Pages.
Mcgarraugh, G., et al., "Physiological Influences on Off-Finger Glucose Testing", Diabetes Technology & Therapeutics, vol. 3, No. 3, 2001, pp. 367-376.
Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Minimed Technologies, "Tape Tips and Other Infusion Site Information", 1995.
Moatti-Sirat, D., et al., "Towards Continuous Glucose Monitoring: In Vivo Evaluation of a Miniaturized Glucose Sensor Implanted for Several Days in Rat Subcutaneous Tissue", Diabetologia, vol. 35, 1992, pp. 224-330.
Ohara, T. J., et al., "Glucose Electrodes Based on Cross-Linked [Os(bpy)$_2$Cl]$^{+/2+}$ Complexed Poly(1-Vinylimidazole) Films", Analytical Chemistry, vol. 65, No. 23, 1993, pp. 3512-3517.
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Poitout, V., et al., "In Vitro and In Vivo Evaluation in Dogs of a Miniaturized Glucose Sensor", ASAIO Transactions, vol. 37, No. 3, 1991, pp. M298-M300.
Quinn, C. P., et al., "Kinetics of Glucose Delivery to Subcutaneous Tissue in Rats Measured with 0.3-mm Amperometric Microsensors", The American Physiological Society, 1995, E155-E161.
Reach, G., et al., "Can Continuous Glucose Monitoring Be Used for the Treatment of Diabetes?", Analytical Chemistry, vol. 64, No. 6, 1992, pp. 381-386.
Rebrin, K., et al., "Automated Feedback Control of Subcutaneous Glucose Concentration in Diabetic Dogs", Diabetologia, vol. 32, 1989, pp. 573-576.
Roe, J. N., et al., "Bloodless Glucose Measurements", Critical Review in Therapeutic Drug Carrier Systems, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidt, F. J., et al., "Calibration of a Wearable Glucose Sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.

(56) References Cited

OTHER PUBLICATIONS

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sternberg, R., et al., "Study and Development of Multilayer Needle-Type Enzyme-Based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A., et al., "Diabetes Mellitus: Biosensors for Research and Management", Biosensors, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.
Velho, G., et al., "Strategies for Calibrating a Subcutaneous Glucose Sensor", Biomedica Biochimica Acta, vol. 48, 1989, pp. 957-964.
Wilson, G. S., et al., "Progress Toward the Development of an Implantable Sensor for Glucose", Clinical Chemistry, vol. 38, No. 9, 1992, pp. 1613-1617.
Ye, L., et al., "High Current Density 'Wired' Quinoprotein Glucose Dehydrogenase Electrode", Analytical Chemistry, vol. 65, No. 3, 1993, pp. 238-241.
Australian Patent Application No. 2007309066, Examination Report dated Aug. 16, 2013.
Australian Patent Application No. 2007309066, Examination Report dated Jul. 12, 2012.
Canadian Patent Application No. 2617192, Examiner's Report dated Oct. 22, 2012.
Canadian Patent Application No. 2624247, Examiner's Report dated Mar. 27, 2013.
Canadian Patent Application No. 2872576, Examiner's Report dated Feb. 17, 2015.
Canadian Patent Application No. 2872576, Examiner's Report dated Feb. 19, 2016.
Chinese Patent Application No. 200780039416.2, Original Language and English Translation of Office Action dated Apr. 25, 2012.
Chinese Patent Application No. 200780039416.2, Original Language and English Translation of Office Action dated Mar. 30, 2011.
Chinese Patent Application No. 20078004373.9, Original Language and English Translation of Notice of Allowance dated May 18, 2011.
Chinese Patent Application No. 20078004373.9, Original Language and English Translation of Office Action dated Apr. 14, 2010.
Chinese Patent Application No. 20088005388.7, Original Language and English Translation of Office Action dated Jul. 25, 2011.
Chinese Patent Application No. 20088005388.7, Original Language and English Translation of Office Action dated May 15, 2012.
European Patent Application No. 08730066.1, Extended European Search Report dated Oct. 5, 2012.
European Patent Application No. EP-06788869.3, Examination Report dated Sep. 25, 2012.
European Patent Application No. EP-06788869.3, Extended European Search Report dated Mar. 18, 2010.
European Patent Application No. EP-06804122.7, Decision to Refuse the Application dated Feb. 25, 2013.
European Patent Application No. EP-06804122.7, Extended European Search Report dated Sep. 28, 2009.
European Patent Application No. EP-06804122.7, Official Letter dated Jan. 25, 2011.
European Patent Application No. EP-06804122.7, Official Letter dated Nov. 30, 2011.
European Patent Application No. EP-06813967.4, Extended European Search Report dated Mar. 4, 2010.
European Patent Application No. EP-06815715.5, Extended European Search Report dated Oct. 30, 2009.
European Patent Application No. EP-06851063.5, Extended European Search Report dated Sep. 21, 2009.
European Patent Application No. EP-07842173.2, Examination Report dated Mar. 21, 2013.
European Patent Application No. EP-07842173.2, Extended European Search Report dated Dec. 29, 2010.
European Patent Application No. EP-07842180.7, Examination Report dated Oct. 23, 2012.
European Patent Application No. EP-07842180.7, Extended Search Report dated Sep. 28, 2009.
European Patent Application No. EP-07842180.7, Official Letter dated Dec. 14, 2011.
European Patent Application No. EP-07842180.7, Second Office Action dated Feb. 23, 2011.
European Patent Application No. EP-07843396.8, Extended European Search Report dated Dec. 22, 2010.
European Patent Application No. EP-07843396.8, Intention to Grant a European Patent dated Sep. 17, 2012.
European Patent Application No. EP-07854298.2, Extended European Search Report dated Mar. 29, 2010.
European Patent Application No. EP-13000104.3, Extended European Search Report dated Mar. 12, 2013.
European Patent Application No. EP-14179905.6, Notice of Opposition filed May 19, 2016.
European Patent Application No. EP-15002441.2, Extended European Search Report dated Dec. 18, 2015.
Israeli Patent Application No. 198329, Original Language and English Translation of Office Action dated Mar. 5, 2012.
Japanese Patent Application No. 2009-534798, Original Language and English Translation of Office Action dated Sep. 25, 2012.
Japanese Patent Application No. 2009-534799, English Translation of Office Action dated Sep. 27, 2011.
Japanese Patent Application No. 2009-534799, Original Language and English Translation of Office Action dated Feb. 19, 2013.
Mexican Patent Application No. MX/a/2009/004322, English Translation of Office Action dated Mar. 11, 2013.
Mexican Patent Application No. MX/a/2009/004322, English Translation of Office Action dated Sep. 19, 2012.
Mexican Patent Application No. MX/a/2009/004398, Original Language and English Translation of Office Action dated Sep. 24, 2012.
PCT Application No. PCT/US2006/029541 International Search Report and Written Opinion of the International Searching Authority dated Apr. 24, 2001.
PCT Application No. PCT/US2006/029541, International Preliminary Report on Patentability and Written Opinion of the International Searching Authority dated Feb. 7, 2008.
PCT Application No. PCT/US2006/033885, International Preliminary Report on Patentability and Written Opinion of the International Searching Authority dated Mar. 13, 2008.
PCT Application No. PCT/US2006/033885, International Search Report and Written Opinion of the International Searching Authority dated Aug. 3, 2007.
PCT Application No. PCT/US2006/037312, International Preliminary Report on Patentability and Written Opinion of the International Searching Authority dated Apr. 11, 2008.
PCT Application No. PCT/US2006/037312, International Search Report and Written Opinion of the International Searching Authority dated Apr. 17, 2007.
PCT Application No. PCT/US2006/037928, International Preliminary Report on Patentability and Written Opinion of the International Searching Authority dated Mar. 19, 2009.
PCT Application No. PCT/US2006/037928, International Search Report and Written Opinion of the International Searching Authority dated Jul. 11, 2008.
PCT Application No. PCT/US2006/062690, International Preliminary Report on Patentability and Written Opinion of the International Searching Authority dated Oct. 7, 2008.
PCT Application No. PCT/US2006/062690, International Search Report and Written Opinion of the International Searching Authority dated Dec. 28, 2006.
PCT Application No. PCT/US2007/078065, International Search Report and Written Opinion of the International Searching Authority dated Apr. 11, 2008.

(56) References Cited

OTHER PUBLICATIONS

PCT Application No. PCT/US2007/078073, International Search Report and Written Opinion of the International Searching Authority dated Apr. 11, 2008.
PCT Application No. PCT/US2007/079774, International Preliminary Report on Patentability and Written Opinion of the International Searching Authority dated Apr. 9, 2009.
PCT Application No. PCT/US2007/079774, International Search Report and Written Opinion of the International Searching Authority dated Mar. 13, 2008.
PCT Application No. PCT/US2007/082114, International Preliminary Report on Patentability and Written Opinion of the International Searching Authority dated May 7, 2009.
PCT Application No. PCT/US2007/082114, International Search Report and Written Opinion of the International Searching Authority dated May 9, 2008.
PCT Application No. PCT/US2007/082121, International Search Report and Written Opinion of the International Searching Authority dated May 9, 2008.
PCT Application No. PCT/US2007/082121, Preliminary Report on Patentability and Written Opinion of the International Searching Authority dated May 7, 2009.
PCT Application No. PCT/US2008/054186, International Preliminary Report on Patentability and Written Opinion of the International Searching Authority dated Aug. 27, 2009.
PCT Application No. PCT/US2008/054186, International Search Report and Written Opinion of the International Searching Authority dated Aug. 8, 2008.
PCT Application No. PCT/US2008/065154, International Preliminary Report on Patentability and Written Opinion of the International Searching Authority dated Dec. 10, 2009.
PCT Application No. PCT/US2008/065154, International Search Report and Written Opinion of the International Searching Authority dated Sep. 3, 2008.
PCT Application No. PCT/US2010/022860, International Preliminary Report on Patentability and Written Opinion of the International Searching Authority dated Aug. 18, 2011.
PCT Application No. PCT/US2010/022860, International Search Report and Written Opinion of the International Searching Authority dated Mar. 10, 2010.
PCT Application No. PCT/US2010/047065, International Preliminary Report on Patentability and Written Opinion of the International Searching Authority dated Mar. 15, 2012.
PCT Application No. PCT/US2010/047065, International Search Report and Written Opinion of the International Searching Authority dated Dec. 21, 2010.
PCT Application No. PCT/US2010/047381, International Preliminary Report on Patentability and Written Opinion of the International Searching Authority dated Mar. 15, 2012.
PCT Application No. PCT/US2010/047381, International Search Report and Written Opinion of the International Searching Authority dated Oct. 15, 2010.
PCT Application No. PCT/US2010/047414, International Preliminary Report on Patentability and Written Opinion of the International Searching Authority dated Mar. 15, 2012.
PCT Application No. PCT/US2010/047414, International Search Report and Written Opinion of the International Searching Authority dated Dec. 27, 2010.
PCT Application No. PCT/US2010/047415, International Preliminary Report on Patentability and Written Opinion of the International Searching Authority dated Mar. 15, 2012.
PCT Application No. PCT/US2010/047415, International Search Report and Written Opinion of the International Searching Authority dated Oct. 25, 2010.
PCT Application No. PCT/US2010/050772, International Preliminary Report on Patentability and Written Opinion of the International Searching Authority dated Apr. 12, 2012.
PCT Application No. PCT/US2010/050772, International Search Report and Written Opinion of the International Searching Authority dated Dec. 3, 2010.
PCT Application No. PCT/US2010/050888, International Preliminary Report on Patentability and Written Opinion of the International Searching Authority dated Apr. 12, 2012.
PCT Application No. PCT/US2010/050888, International Search Report and Written Opinion of the International Searching Authority dated Nov. 29, 2010.
PCT Application No. PCT/US2010/051861, International Preliminary Report on Patentability and Written Opinion of the International Searching Authority dated Apr. 19, 2012.
PCT Application No. PCT/US2010/051861, International Search Report and Written Opinion of the International Searching Authority dated Nov. 30, 2010.
Russian Patent Application No. 2009-119430, Original Language and English Translation of Office Action dated Jun. 5, 2011.
Russian Patent Application No. 2009135048, Original Language and English Translation of Office Action dated Dec. 20, 2011.
U.S. Appl. No. 11/026,766, Office Action dated Apr. 28, 2011.
U.S. Appl. No. 11/026,766, Office Action dated Apr. 4, 2009.
U.S. Appl. No. 11/026,766, Office Action dated Dec. 24, 2009.
U.S. Appl. No. 11/026,766, Office Action dated Feb. 8, 2012.
U.S. Appl. No. 11/026,766, Office Action dated Jan. 26, 2007.
U.S. Appl. No. 11/026,766, Office Action dated Jul. 12, 2013.
U.S. Appl. No. 11/026,766, Office Action dated Jul. 21, 2008.
U.S. Appl. No. 11/026,766, Office Action dated May 9, 2006.
U.S. Appl. No. 11/026,766, Office Action dated Oct. 15, 2007.
U.S. Appl. No. 11/026,766, Office Action dated Oct. 19, 2011.
U.S. Appl. No. 11/026,766, Office Action dated Oct. 28, 2010.
U.S. Appl. No. 11/027,230, Advisory Action dated Aug. 27, 2012.
U.S. Appl. No. 11/027,230, Advisory Action dated Jul. 29, 2010.
U.S. Appl. No. 11/027,230, Notice of Allowance dated Aug. 14, 2013.
U.S. Appl. No. 11/027,230, Office Action dated Apr. 11, 2012.
U.S. Appl. No. 11/027,230, Office Action dated Apr. 24, 2013.
U.S. Appl. No. 11/027,230, Office Action dated Dec. 4, 2009.
U.S. Appl. No. 11/027,230, Office Action dated Jun. 24, 2008.
U.S. Appl. No. 11/027,230, Office Action dated Mar. 20, 2009.
U.S. Appl. No. 11/027,230, Office Action dated May 6, 2010.
U.S. Appl. No. 11/027,230, Office Action dated Oct. 1, 2012.
U.S. Appl. No. 11/192,773, Advisory Action dated Aug. 19, 2009.
U.S. Appl. No. 11/192,773, Office Action dated Apr. 4, 2007.
U.S. Appl. No. 11/192,773, Office Action dated Apr. 16, 2009.
U.S. Appl. No. 11/192,773, Office Action dated Aug. 2, 2011.
U.S. Appl. No. 11/192,773, Office Action dated Dec. 12, 2007.
U.S. Appl. No. 11/192,773, Office Action dated Dec. 17, 2009.
U.S. Appl. No. 11/192,773, Office Action dated Jan. 31, 2012.
U.S. Appl. No. 11/192,773, Office Action dated Jul. 16, 2010.
U.S. Appl. No. 11/192,773, Office Action dated Jul. 21, 2008.
U.S. Appl. No. 11/192,773, Office Action dated Mar. 29, 2013.
U.S. Appl. No. 11/192,773, Office Action dated Oct. 28, 2010.
U.S. Appl. No. 11/216,932, Notice of Allowance dated Mar. 11, 2010.
U.S. Appl. No. 11/216,932, Office Action dated Feb. 25, 2008.
U.S. Appl. No. 11/216,932, Office Action dated Jul. 9, 2008.
U.S. Appl. No. 11/216,932, Office Action dated May 24, 2007.
U.S. Appl. No. 11/240,257, Notice of Allowance dated Dec. 16, 2010.
U.S. Appl. No. 11/240,257, Office Action dated Apr. 17, 2009.
U.S. Appl. No. 11/240,257, Office Action dated Dec. 24, 2009.
U.S. Appl. No. 11/240,257, Office Action dated Jul. 12, 2010.
U.S. Appl. No. 11/240,257, Office Action dated Jun. 27, 2008.
U.S. Appl. No. 11/240,257, Office Action dated Oct. 18, 2010.
U.S. Appl. No. 11/240,259, Notice of Allowance dated Jun. 3, 2013.
U.S. Appl. No. 11/240,259, Office Action dated Jun. 5, 2009.
U.S. Appl. No. 11/240,259, Office Action dated Nov. 29, 2007.
U.S. Appl. No. 11/240,259, Office Action dated Nov. 30, 2009.
U.S. Appl. No. 11/240,259, Office Action dated Oct. 6, 2008.
U.S. Appl. No. 11/365,334, Advisory Action dated Jul. 29, 2009.
U.S. Appl. No. 11/365,334, Notice of Allowance dated Jul. 14, 2011.
U.S. Appl. No. 11/365,334, Office Action dated Apr. 20, 2009.
U.S. Appl. No. 11/365,334, Office Action dated Dec. 28, 2009.
U.S. Appl. No. 11/365,334, Office Action dated Feb. 7, 2011.
U.S. Appl. No. 11/365,334, Office Action dated Jun. 30, 2008.

(56) References Cited

OTHER PUBLICATIONS

U.S. Appl. No. 11/365,334, Office Action dated May 14, 2010.
U.S. Appl. No. 11/380,883, Office Action dated Jul. 19, 2010.
U.S. Appl. No. 11/380,883, Office Action dated Jul. 7, 2008.
U.S. Appl. No. 11/380,883, Office Action dated Nov. 12, 2009.
U.S. Appl. No. 11/380,883, Office Action dated Oct. 3, 2008.
U.S. Appl. No. 11/530,472, Advisory Action dated Apr. 20, 2009.
U.S. Appl. No. 11/530,472, Advisory Action dated Apr. 21, 2010.
U.S. Appl. No. 11/530,472, Notice of Allowance dated Aug. 17, 2012.
U.S. Appl. No. 11/530,472, Office Action dated Dec. 14, 2010.
U.S. Appl. No. 11/530,472, Office Action dated Feb. 2, 2010.
U.S. Appl. No. 11/530,472, Office Action dated Jan. 14, 2008.
U.S. Appl. No. 11/530,472, Office Action dated Jun. 1, 2012.
U.S. Appl. No. 11/530,472, Office Action dated May 14, 2009.
U.S. Appl. No. 11/530,472, Office Action dated May 18, 2011.
U.S. Appl. No. 11/530,472, Office Action dated Nov. 21, 2008.
U.S. Appl. No. 11/530,472, Office Action dated Sep. 10, 2011.
U.S. Appl. No. 11/530,473, Office Action dated Dec. 11, 2009.
U.S. Appl. No. 11/530,473, Office Action dated Jan. 10, 2008.
U.S. Appl. No. 11/530,473, Office Action dated Jun. 25, 2010.
U.S. Appl. No. 11/530,473, Office Action dated May 14, 2009.
U.S. Appl. No. 11/530,473, Office Action dated Oct. 6, 2008.
U.S. Appl. No. 11/535,983, Notice of Allowance dated Feb. 19, 2010.
U.S. Appl. No. 11/535,983, Office Action dated Jun. 26, 2009.
U.S. Appl. No. 11/535,983, Office Action dated Oct. 3, 2008.
U.S. Appl. No. 11/552,065, Advisory Action dated Sep. 5, 2012.
U.S. Appl. No. 11/552,065, Office Action dated Jun. 28, 2012.
U.S. Appl. No. 11/552,065, Office Action dated Nov. 17, 2011.
U.S. Appl. No. 11/552,072, Office Action dated Jan. 20, 2010.
U.S. Appl. No. 11/552,072, Office Action dated Jul. 23, 2009.
U.S. Appl. No. 11/552,072, Office Action dated Oct. 3, 2008.
U.S. Appl. No. 11/617,698, Notice of Allowance dated May 24, 2013.
U.S. Appl. No. 11/617,698, Office Action dated Dec. 17, 2009.
U.S. Appl. No. 11/617,698, Office Action dated Jun. 21, 2010.
U.S. Appl. No. 11/617,698, Office Action dated Jun. 26, 2009.
U.S. Appl. No. 11/617,698, Office Action dated Nov. 29, 2010.
U.S. Appl. No. 11/617,698, Office Action dated Oct. 2, 2012.
U.S. Appl. No. 11/617,698, Office Action dated Oct. 3, 2008.
U.S. Appl. No. 12/032,593, Advisory Action dated Nov. 24, 2010.
U.S. Appl. No. 12/032,593, Office Action dated Mar. 26, 2010.
U.S. Appl. No. 12/032,593, Office Action dated Sep. 17, 2010.
U.S. Appl. No. 12/129,573, Notice of Allowance dated Aug. 22, 2013.
U.S. Appl. No. 12/129,573, Office Action dated Apr. 13, 2012.
U.S. Appl. No. 12/129,573, Office Action dated Mar. 11, 2013.
U.S. Appl. No. 12/129,573, Office Action dated Oct. 22, 2012.
U.S. Appl. No. 12/129,573, Office Action dated Sep. 29, 2011.
U.S. Appl. No. 12/571,349, Office Action dated Apr. 29, 2011.
U.S. Appl. No. 12/571,349, Office Action dated Nov. 10, 2010.
U.S. Appl. No. 12/571,349, Office Action dated Oct. 11, 2013.
U.S. Appl. No. 12/795,634, Notice of Allowance dated Oct. 2, 2013.
U.S. Appl. No. 12/795,634, Notice of Allowance dated Sep. 16, 2013.
U.S. Appl. No. 12/795,634, Office Action dated May 23, 2013.
U.S. Appl. No. 12/826,662, Advisory Action dated Sep. 12, 2012.
U.S. Appl. No. 12/826,662, Office Action dated Dec. 22, 2011.
U.S. Appl. No. 12/826,662, Office Action dated Jul. 2, 2012.
U.S. Appl. No. 12/826,662, Office Action dated Nov. 4, 2013.
U.S. Appl. No. 12/870,818, Office Action dated May 23, 2013.
U.S. Appl. No. 12/870,818, Office Action dated Nov. 29, 2013.
U.S. Appl. No. 12/873,301, Office Action dated Aug. 27, 2012.
U.S. Appl. No. 12/873,301, Office Action dated Oct. 29, 2013.
U.S. Appl. No. 12/873,302, Office Action dated Mar. 14, 2013.
U.S. Appl. No. 12/873,302, Office Action dated Oct. 15, 2012.
U.S. Appl. No. 12/873,302, Office Action dated Sep. 12, 2013.
U.S. Appl. No. 12/893,974, Office Action dated Dec. 19, 2013.
U.S. Appl. No. 12/893,974, Office Action dated Mar. 28, 2013.
U.S. Appl. No. 13/022,616, Office Action dated Feb. 26, 2014.
U.S. Appl. No. 13/252,118, Office Action dated May 19, 2013.
U.S. Appl. No. 13/717,501, Office Action dated Jan. 10, 2014.
U.S. Patent Reexamination U.S. Appl. No. 90/008,172, Request for Reexamination of U.S. Pat. No. 6,990,366, filed Aug. 16, 2006.
U.S. Patent Reexamination U.S. Appl. No. 90/008,457, Notice of Intent to Issue Reexamination Certificate dated Mar. 13, 2008.
U.S. Patent Reexamination U.S. Appl. No. 90/008,457, Order Granting Request for Reexamination dated Feb. 23, 2007.
U.S. Patent Reexamination U.S. Appl. No. 90/008,457, Request for Reexamination of U.S. Pat. No. 6,990,366, filed Jan. 23, 2007.
U.S. Patent Reexamination U.S. Appl. Nos. 90/009,328 & 90/009,328, Notice of Intent to Issue Reexamination Certificate dated Nov. 20, 2009.
U.S. Patent Reexamination U.S. Appl. Nos. 90/009,328 & 90/009,328, Office Action dated Aug. 4, 2009.
U.S. Patent Reexamination U.S. Appl. Nos. 90/009,328 & 90/009,328, Office Action dated Sep. 30, 2009.
U.S. Patent Reexamination U.S. Appl. No. 90/009,104, Office Action dated Oct. 16, 2008.
U.S. Patent Reexamination U.S. Appl. No. 90/009,104, Order Granting Request for Reexamination dated Jun. 5, 2008.
U.S. Patent Reexamination U.S. Appl. No. 90/009,104, Request for Reexamination of U.S. Pat. No. 6,990,366 filed Apr. 8, 2008.
U.S. Patent Reexamination U.S. Appl. No. 90/009,328, Order Granting Request for Reexamination dated Dec. 9, 2008.
U.S. Patent Reexamination U.S. Appl. No. 90/009,328, Request for Reexamination of U.S. Pat. No. 6,990,366 filed Nov. 10, 2008.
U.S. Patent Reexamination U.S. Appl. No. 90/010,791, Notice of Intent to Issue Reexamination Certificate dated May 17, 2011.
U.S. Patent Reexamination U.S. Appl. No. 90/010,791, Office Action dated Dec. 17, 2010.
U.S. Patent Reexamination U.S. Appl. No. 90/010,791, Office Action dated May 28, 2010.
U.S. Patent Reexamination U.S. Appl. No. 90/010,791, Order Granting Request for Reexamination dated Feb. 22, 2010.
U.S. Patent Reexamination U.S. Appl. No. 90/010,791, Request for Reexamination of U.S. Pat. No. 6,990,366 filed Dec. 22, 2009.
U.S. Patent Reexamination U.S. Appl. No. 90/011,730, Notice of Intent to Issue Reexam Certificate for U.S. Pat. No. 6,990,366 dated Apr. 5, 2012.
U.S. Patent Reexamination U.S. Appl. No. 90/011,730, Office Action dated Jan. 11, 2012.
U.S. Patent Reexamination U.S. Appl. No. 90/011,730, Order Granting Request for Reexamination of U.S. Pat. No. 6,990,366 dated Aug. 24, 2011
U.S. Patent Reexamination U.S. Appl. No. 90/011,730, Request for Reexamination of U.S. Pat. No. 6,990,366 filed Jun. 3, 2011.
U.S. Patent Reexamination U.S. Appl. No. 95/002,113, Order Denying Request for Reexamination of U.S. Pat. No. 6,990,366 dated Nov. 13, 2012.
U.S. Patent Reexamination U.S. Appl. No. 95/002,113, Petition for Review of the Order Denying Request Reexamination of U.S. Pat. No. 6,990,366 dated Dec. 13, 2012.
U.S. Patent Reexamination U.S. Appl. No. 95/002,113, Request for Reexamination of U.S. Pat. No. 6,990,366 filed Aug. 30, 2012.
U.S. Patent Reexamination U.S. Appl. No. 95/002,162, Order Denying Request for Reexamination of U.S. Pat. No. 8,175,673 dated Nov. 13, 2012.
U.S. Patent Reexamination U.S. Appl. No. 95/002,162, Petition for Review of the Order Denying Request Reexamination of U.S. Pat. No. 8,175,673 dated Dec. 13, 2012.
U.S. Patent Reexamination U.S. Appl. No. 95/002,162, Request for Reexamination of U.S. Pat. No. 8,175,673 filed Sep. 7, 2012.

\* cited by examiner

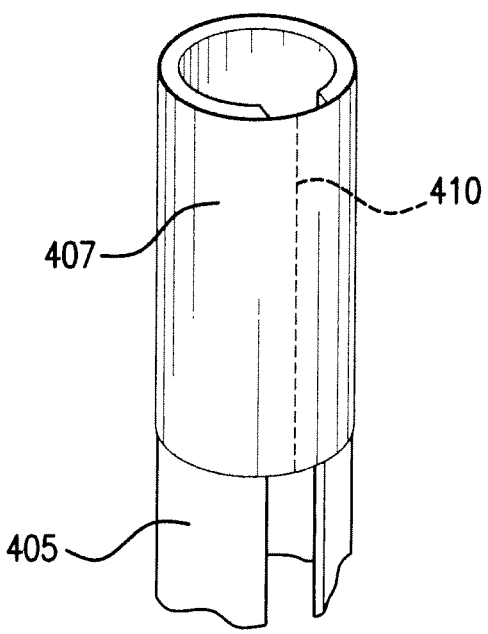
FIG.12
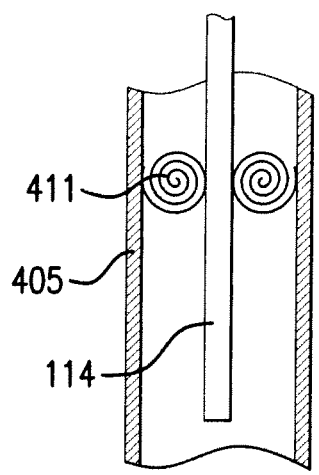 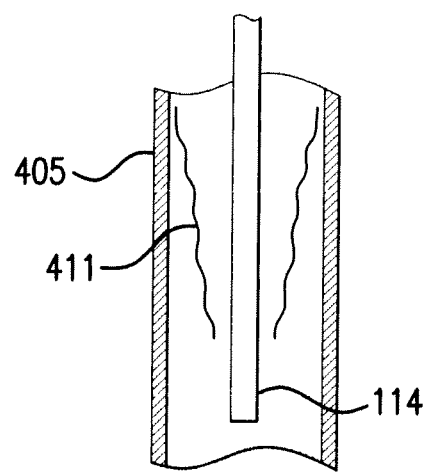
FIG.13  FIG.14

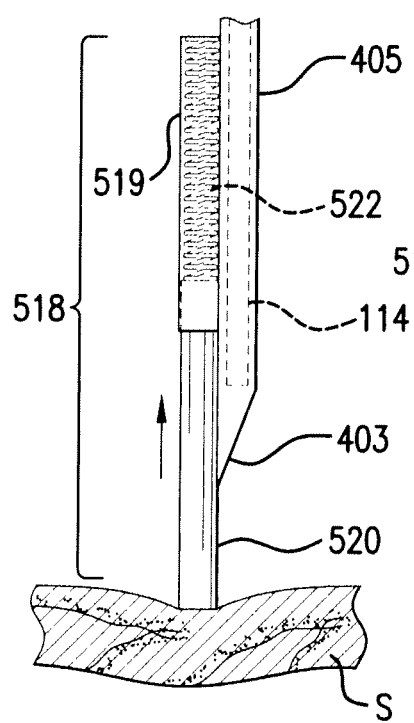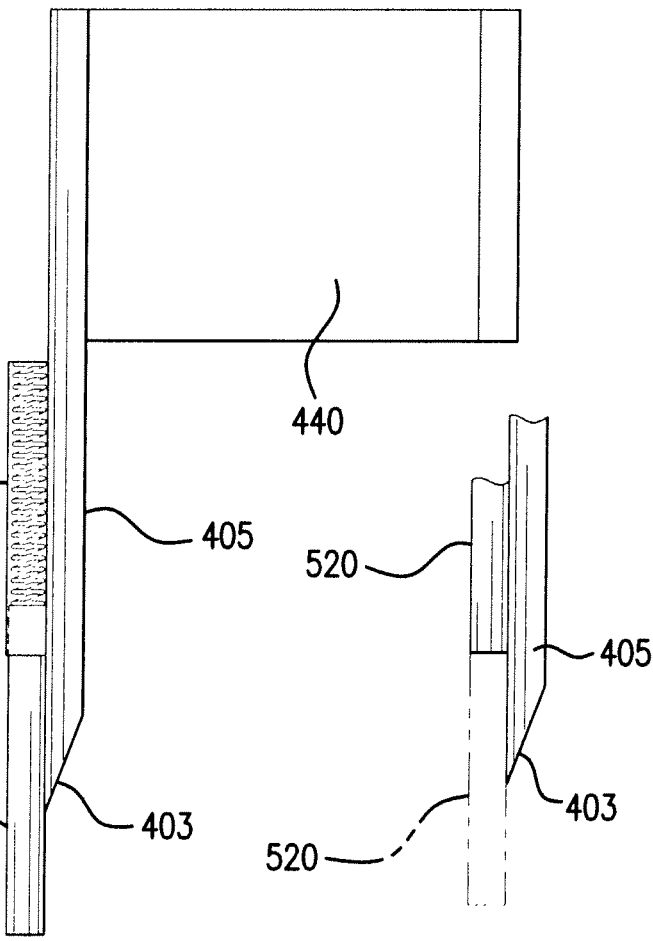
FIG.23  FIG.24  FIG.25
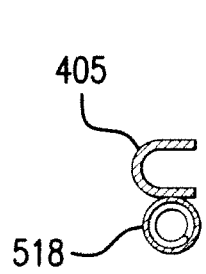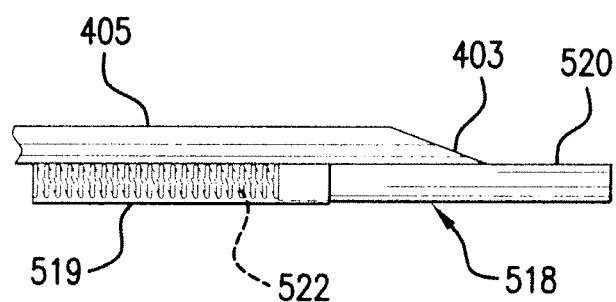
FIG.26  FIG.27

SENSOR INSERTER HAVING INTRODUCER

RELATED APPLICATIONS

The present application is a continuation of U.S. patent application Ser. No. 14/040,674 filed Sep. 28, 2013, which is a continuation-in-part of U.S. patent application Ser. No. 12/893,974 filed Sep. 29, 2010, now abandoned, which claims priority to U.S. Provisional Application No. 61/246,825 filed Sep. 29, 2009, the disclosures of each of which are incorporated herein by reference for all purposes. The present application is also a continuation-in-part of U.S. patent application Ser. No. 12/795,634 filed Jun. 7, 2010, now U.S. Pat. No. 8,602,991, which is a continuation of U.S. patent application Ser. No. 11/216,932 filed Aug. 30, 2005, now U.S. Pat. No. 7,731,657, the disclosures of each of which are incorporated herein by reference for all purposes. The present application is also a continuation-in-part of U.S. patent application Ser. No. 13/022,616 filed Feb. 7, 2011, which is a continuation of U.S. patent application Ser. No. 11/240,257 filed Sep. 30, 2005, now U.S. Pat. No. 7,883,464, the disclosures of each of which are incorporated herein by reference for all purposes. The present application is also a continuation-in-part of U.S. patent application Ser. No. 11/552,065 filed Oct. 23, 2006, now U.S. Pat. No. 9,259,175, the disclosure of which is incorporated herein by reference for all purposes. The present application is also a continuation-in-part of U.S. patent application Ser. No. 12/129,573 filed May 29, 2008, now U.S. Pat. No. 8,613,703, which claims priority to U.S. Provisional Application No. 60/941,060 filed May 31, 2007, the disclosures of each of which are incorporated herein by reference for all purposes. The present application is also a continuation-in-part of U.S. patent application Ser. No. 12/870,818 filed Aug. 28, 2010, now abandoned, which claims priority to U.S. Provisional Application No. 61/238,159 filed Aug. 29, 2009, the disclosures of each of which are incorporated herein by reference for all purposes. The present application is also a continuation-in-part of U.S. patent application Ser. No. 12/873,301 filed Aug. 31, 2010, now abandoned, which claims priority to U.S. Provisional Application No. 61/238,494 filed Aug. 31, 2009, the disclosures of each of which are incorporated herein by reference for all purposes. The present application is also a continuation-in-part of U.S. patent application Ser. No. 12/873,302 filed Aug. 31, 2010, now abandoned, which claims priority to U.S. Provisional Application Nos. 61/238,537 filed Aug. 31, 2009 and 61/238,483 filed Aug. 31, 2009, the disclosures of each of which are incorporated herein by reference for all purposes. The present application is also a continuation-in-part of U.S. patent application Ser. No. 13/171,401 filed Jun. 28, 2011, now U.S. Pat. No. 9,572,534, which claims priority to U.S. Provisional Application No. 61/359,816 filed Jun. 29, 2010, the disclosures of each of which are incorporated herein by reference for all purposes. The present application is also a continuation-in-part of U.S. patent application Ser. No. 13/434,804 filed Mar. 29, 2012, now U.S. Pat. No. 9,743,862, which claims priority to U.S. Provisional Application No. 61/470,454 filed Mar. 31, 2011, the disclosures of each of which are incorporated herein by reference for all purposes. The present application is also a continuation-in-part of U.S. patent application Ser. No. 11/026,766 filed Dec. 29, 2004, now abandoned, the disclosure of which is incorporated herein by reference for all purposes. The present application is also a continuation-in-part of U.S. patent application Ser. No. 13/252,118 filed Oct. 3, 2011, now U.S. Pat. No. 9,364,149, which is a continuation of U.S. patent application Ser. No. 11/365,334 filed Feb. 28, 2006, now U.S. Pat. No. 8,029,441, the disclosures of each of which are incorporated herein by reference for all purposes. The present application is also a continuation-in-part of U.S. patent application Ser. No. 13/970,397 filed Aug. 19, 2013, now U.S. Pat. No. 9,480,421, which is a continuation of U.S. patent application Ser. No. 11/240,259 filed Sep. 30, 2005, now U.S. Pat. No. 8,512,243, the disclosures of each of which are incorporated herein by reference for all purposes. The present application is also a continuation-in-part of U.S. patent application Ser. No. 11/530,473 filed Sep. 10, 2006, now U.S. Pat. No. 9,398,882, which is a continuation-in-part of U.S. patent application Ser. No. 11/240,259 filed Sep. 30, 2005, now U.S. Pat. No. 8,512,243, the disclosures of each of which are incorporated herein by reference for all purposes. The present application is also a continuation-in-part of U.S. patent application Ser. No. 11/380,883 filed Apr. 28, 2006, now abandoned, the disclosure of which is incorporated herein by reference for all purposes. The present application is also a continuation-in-part of U.S. patent application Ser. No. 13/717,501 filed Dec. 17, 2012, now U.S. Pat. No. 8,862,198, which is a continuation of U.S. patent application Ser. No. 11/530,472 filed Sep. 10, 2006, now U.S. Pat. No. 8,333,714, the disclosures of each of which are incorporated herein by reference for all purposes. The present application is also a continuation-in-part of U.S. patent application Ser. No. 11/192,773 filed Jul. 29, 2005, now abandoned, the disclosure of which is incorporated herein by reference for all purposes. The present application is also a continuation-in-part of U.S. patent application Ser. No. 11/552,072 filed Oct. 23, 2006, now U.S. Pat. No. 9,788,771, the disclosure of which is incorporated herein by reference for all purposes. The present application is also a continuation-in-part of U.S. patent application Ser. No. 11/027,230 filed Dec. 29, 2004, now U.S. Pat. No. 8,571,624, the disclosure of which is incorporated herein by reference for all purposes. The present application is also a continuation-in-part of U.S. patent application Ser. No. 12/895,015 filed Sep. 30, 2010, now U.S. Pat. No. 9,351,669, which claims priority to U.S. Provisional Application No. 61/247,516 filed Sep. 30, 2009, the disclosures of each of which are incorporated herein by reference for all purposes. The present application is also a continuation-in-part of U.S. patent application Ser. No. 11/617,698 filed Dec. 28, 2006, now U.S. Pat. No. 8,545,403, which claims priority to U.S. Provisional Application No. 60/754,870 filed Dec. 28, 2005, the disclosures of each of which are incorporated herein by reference for all purposes. The present application is also a continuation-in-part of U.S. patent application Ser. No. 12/571,349 filed Sep. 30, 2009, now U.S. Pat. No. 8,852,101, which is a continuation of U.S. patent application Ser. No. 11/535,983 filed Sep. 28, 2006, now U.S. Pat. No. 7,697,967, which claims priority to U.S. Provisional Application No. 60/754,870 filed Dec. 28, 2005, the disclosures of each of which are incorporated herein by reference for all purposes. The present application is also a continuation-in-part of U.S. patent application Ser. No. 12/032,593 filed Feb. 15, 2008, now U.S. Pat. No. 9,636,450, which claims priority to U.S. Provisional Application No. 60/890,497 filed Feb. 19, 2007, the disclosures of each of which are incorporated herein by reference for all purposes.

FIELD OF THE DISCLOSURE

The present disclosure relates to a sensor delivery unit. More particularly, the present disclosure relates to a sensor inserter having a safety member to impede actuation of the inserter. The present disclosure also relates to an introducer having a holding member configured to releasably retain a sensor, such as an analyte sensor. The introducer can further comprise a compressible member configured to tent the skin and puncture the skin to a reduced depth during insertion of a sensor. The present disclosure also relates to a method of arming the sensor delivery unit.

BACKGROUND

Diabetes Mellitus is an incurable chronic disease in which the body does not produce or properly utilize insulin. Insulin is a hormone produced by the pancreas that regulates blood sugar (glucose). In particular, when blood sugar levels rise, e.g., after a meal, insulin lowers the blood sugar levels by facilitating blood glucose to move from the blood into the body cells. Thus, when the pancreas does not produce sufficient insulin (a condition known as Type I Diabetes) or does not properly utilize insulin (a condition known as Type II Diabetes), the blood glucose remains in the blood resulting in hyperglycemia or abnormally high blood sugar levels.

The vast and uncontrolled fluctuations in blood glucose levels in people suffering from diabetes cause long-term, serious complications. Some of these complications include blindness, kidney failure, and nerve damage. Additionally, it is known that diabetes is a factor in accelerating cardiovascular diseases such as atherosclerosis (hardening of the arteries), leading to stroke, coronary heart disease, and other diseases. Accordingly, one important and universal strategy in managing diabetes is to control blood glucose levels.

The first step in managing blood glucose levels is testing and monitoring blood glucose levels by using conventional techniques, such as drawing blood samples, applying the blood to a test strip, and determining the blood glucose level using colorimetric, electrochemical, or photometric test meters. Another more recent technique for monitoring glucose levels is by using commercially available continuous glucose monitoring systems.

In accordance with the monitoring of glucose levels, a sensor is typically subcutaneously or transcutaneously positioned under the skin of a user. In this regard, a sensor inserter assembly, which can be preloaded with a sensor, is employed to insert the sensor through the skin of a user. A new sensor is generally implanted under the user's skin every three to seven days. Thus, easy to use sensor inserter assemblies causing reduced trauma to the skin during use are desired.

SUMMARY

In certain embodiments, a sensor insertion assembly is provided that includes an inserter housing, an introducer including a body portion having a proximal end and a distal end and a shaft portion comprising a channel and a distal end, the shaft portion extending downwardly from an edge of the body portion, the shaft portion including a holding member disposed along a length of the channel, the holding member configured to substantially releasably retain a sensor, an on-body electronics unit, wherein the introducer is configured for insertion of the sensor through an aperture in the on-body electronics unit prior to insertion through skin and a drive mechanism included in the inserter housing and operatively coupled to the introducer that drives the introducer and retained sensor through the skin.

In certain embodiments, the introducer holding member may include one or more rolling members disposed along a length of the shaft portion, the rolling members configured to contact and releasably retain the sensor. The introducer rolling members may be configured to rotate. The sensor retained by the shaft portion of the introducer may be displaced from the shaft portion upon rotation of the rolling members. The introducer rolling members may be disposed within the channel. The introducer rolling members may be disposed within a sidewall of the channel. The introducer shaft portion may include an aperture formed in the channel, and the sensor may include a flange extending from an edge of the sensor, the flange disposed in the aperture formed in the channel. The aperture may include a section configured to be wider than the width of a sensor flange such that the sensor may be displaced from the shaft. The introducer holding member may comprise a sponge material disposed along the channel of the shaft portion, the sponge material configured to provide a soft interference fit with a sensor disposed in the shaft portion.

In certain embodiments, the introducer shaft portion is substantially hollow. The introducer shaft portion may be configured to retain at least a portion of the sensor substantially subcutaneously when the shaft portion is removed from a skin layer. The introducer distal end may include a tapered end configured to pierce the skin layer and at least a portion of the sensor may be substantially retained within the shaft portion while the tapered end is piercing through the skin layer. The sensor may be substantially contemporaneously transcutaneously introduced through the skin layer when the tapered end of the shaft portion is transcutaneously introduced to the skin layer. In certain embodiments, the sensor includes an analyte sensor. The analyte sensor may be a glucose sensor. The introducer may be configured to position the analyte sensor in fluid contact with an analyte of a user.

In certain embodiments, the introducer may include a compressible member having a distal end, the compressible member attached to a lateral side of the introducer shaft portion, wherein the distal end of the compressible member is distal to the distal end of the introducer shaft portion. The compressible member may be configured to retract to allow the sharp to penetrate skin of a user.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 12 is a perspective view of a shaft portion having one or more holding members in accordance with the disclosed subject matter;

FIG. 13 is a sectional view of a shaft portion having one or more holding members in accordance with the disclosed subject matter in a first configuration;

FIG. 14 is a sectional view of a shaft portion having one or more holding member in accordance with the disclosed subject matter in a second configuration;

FIG. 23 is a side view of a shaft portion comprising a compressible member in accordance with the disclosed subject matter in a second configuration;

FIG. 24 is an enlarged side view of a shaft portion of FIG. 23 in accordance with the disclosed subject matter in a second configuration;

FIG. 25 is a partial side view of a shaft portion of FIG. 23 in accordance with the disclosed subject matter in a second configuration;

FIG. 26 is a sectional view of a shaft portion of FIG. 23 in accordance with the disclosed subject matter in a second configuration;

FIG. 27 is a side view of a shaft portion of FIG. 23 in accordance with the disclosed subject matter in a second configuration;

DETAILED DESCRIPTION OF EXEMPLARY EMBODIMENTS

Figure 1:
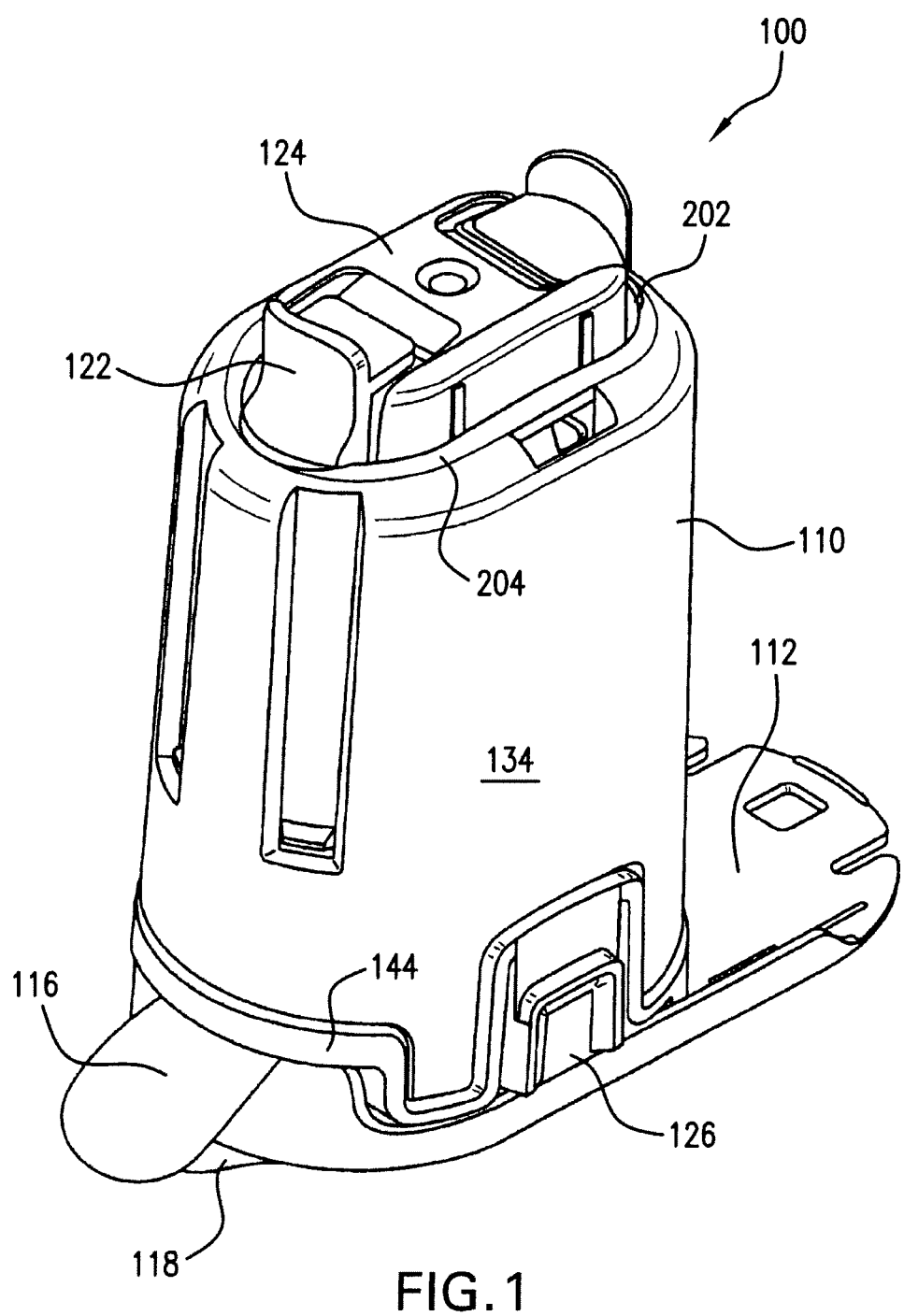
FIG. 1 is a perspective view showing a sensor inserter and adhesive mount constructed in accordance with the disclosed subject matter.
Figure 2:
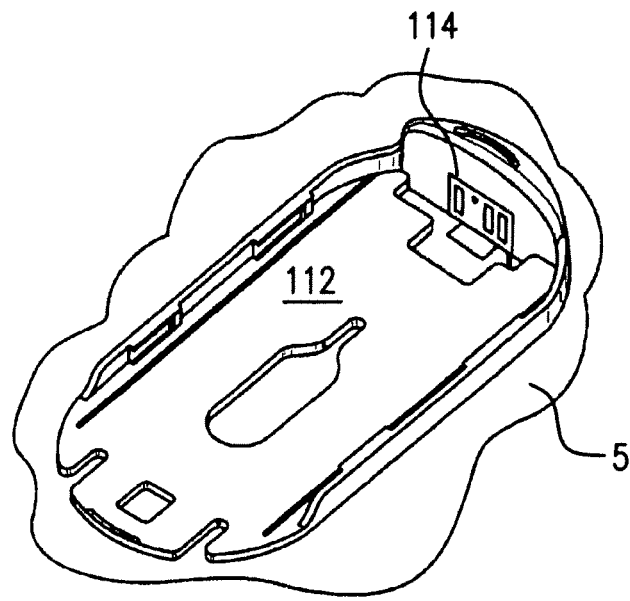
FIG. 2 is a perspective view of the adhesive mount and sensor attached to the user's skin in accordance with the disclosed subject matter.

A detailed description of the disclosure is provided herein. It should be understood, in connection with the following description, that the subject matter is not limited to particular embodiments described, as the particular embodiments of the subject matter may of course vary. It is also to be understood that the terminology used herein is for the purpose of describing particular embodiments only, and is not intended to be limiting, since the scope of the disclosed subject matter will be limited only by the appended claims.

Where a range of values is provided, it is understood that each intervening value between the upper and lower limit of that range and any other stated or intervening value in that stated range, is encompassed within the disclosed subject matter. Every range stated is also intended to specifically disclose each and every "sub-rang" of the stated range. That is, each and every range smaller than the outside range specified by the outside upper and outside lower limits given for a range, whose upper and lower limits are within the range from said outside lower limit to said outside upper limit (unless the context clearly dictates otherwise), is also to be understood as encompassed within the disclosed subject matter, subject to any specifically excluded range or limit within the stated range. Where a range is stated by specifying one or both of an upper and lower limit, ranges excluding either or both of those stated limits, or including one or both of them, are also encompassed within the disclosed subject matter, regardless of whether or not words such as "from", "to", "through", or "including" are or are not used in describing the range.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated herein by reference in its entirety herein for all purposes, including without limitation to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior disclosure. Further, the dates of publication provided may be different from the actual publication dates, which may need to be independently confirmed.

As used herein and in the appended claims, the singular forms "a", "an", and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order which is logically possible. Reference to a singular item, includes the possibility that there are plural of the same item present. When two or more items (for example, elements or processes) are referenced by an alternative "or", this indicates that either could be present separately or any combination of them could be present together except where the presence of one necessarily excludes the other or others.

Various exemplary embodiments of the analyte monitoring system and methods of the present disclosure are described in further detail below. Although the present disclosure is described primarily with respect to a glucose monitoring system, each aspect of the present disclosure is not intended to be limited to the particular embodiment so described. Accordingly, it is to be understood that such description should not be construed to limit the scope of the present disclosure, and it is to be understood that the analyte monitoring system can be configured to monitor a variety of analytes, as described below. Further, section headers, where provided, are merely for the convenience of the reader and are not to be taken as limiting the scope of the present disclosure in any way, as it will be understood that certain elements and features of the present disclosure have more than one function and that aspects of the present disclosure and particular elements are described throughout the specification.

A. Overview

The present disclosure is generally directed to an analyte monitoring system including an apparatus, such as an inserter, configured to insert various devices into the body of a subject, such as for example, an analyte sensor, an infusion set, or a lancing device.

Certain classes of analyte monitoring systems are provided in small, lightweight, battery-powered and electronically-controlled systems. Such systems may be configured to detect signals indicative of in vivo analyte levels using an electrochemical sensor, and collect such signals, with or without processing the signal. In some embodiments, the portion of the system that performs this initial processing may be configured to provide the raw or initially processed data to another unit for further collection and/or processing. Such provision of data may be effected, for example, via a wired connection, such as an electrical, or via a wireless connection, such as an IR or RF connection.

Certain analyte monitoring systems for in vivo measurement employ a sensor that measures analyte levels in interstitial fluids under the surface of the subject's skin. These may be inserted partially through the skin or positioned entirely under the skin. A sensor in such a system may operate as an electrochemical cell. Such a sensor may use any of a variety of electrode configurations, such as a three-electrode configuration (e.g., with "working", "reference" and "counter" electrodes), driven by a controlled potential (potentiostat) analog circuit, a two-electrode system configuration (e.g., with only working and counter electrodes), which may be self-biasing and/or self-powered, and/or other configurations. In some embodiments, the sensor may be positioned within a blood vessel.

In certain systems, the analyte sensor is in communication with a sensor control unit. As used in this disclosure, an on-body unit sometimes refers to such a combination of an analyte sensor with such a sensor control unit. The analyte monitoring system may include an on-body unit including a sensor and a monitor unit. Exemplary embodiments of combination analyte sensor and sensor control unit configurations are further disclosed in, among others, U.S. patent application Ser. Nos. 12/873,301 and 11/530,473, now U.S. Pat. No. 9,398,882, the disclosures of each of which are incorporated herein by reference for all purposes. In some embodiments, the on-body unit includes electronics configured to process the signal generated by the sensor and may further include a transmitter, transceiver, or other communications electronics to provide the processed data to the monitor unit via a communication link between the on-body unit and the monitor unit.

Analyte monitoring systems, in some embodiments, include an adhesive mounting unit for adhering the on-body unit to a patient's skin. Exemplary mounting units can be found in, among others, U.S. patent application Ser. Nos. 12/873,302, 13/171,401, now U.S. Pat. No. 9,572,534, and Ser. No. 11/027,230, now U.S. Pat. No. 8,571,624, the disclosures of each of which are incorporated herein by reference for all purposes. In certain embodiments, mounting units include a base module in addition to an adhesive. The base module may be configured to physically couple with the on-body unit electronics for adhesive mounting of the on-body unit electronics to the patient. Examples of such coupling embodiments can be found in, among others, Ser. No. 12/895,015, now U.S. Pat. No. 9,351,669, and Ser. No. 11/365,334, now U.S. Pat. No. 8,029,441, the disclosures of each of which are incorporated herein by reference for all purposes. In some embodiments the mounting unit may also include a temperature sensing module to monitor the temperature of the skin of the patient, such as disclosed in Ser. No. 11/026,766, the disclosure of which is incorporated herein by reference.

In certain embodiments, the on-body unit is placed on the skin of the patient prior to insertion of the sensor through the skin. In such embodiments, the sensor may be inserted through an aperture in the on-body unit prior to penetration of skin. Exemplary disclosures of these embodiments can be found in, among others, U.S. Publication Nos. 2011/0213225, 2010/0198034, 2010/0324392, 2011/0319729, 2011/0288574, 2012/0010642 and 2013/0150691, the disclosures of which are incorporated herein by reference for all purposes.

The monitor unit can include a display for displaying or communicating information to the user of the analyte monitoring system or the user's health care provider or another. The monitor unit is also referred to in this disclosure as a "receiver unit" or "receiver device", or in some contexts, depending on the usage, as a "display unit," "handheld unit," or "meter". In some embodiments, receiver may also include buttons and/or scroll wheel which allow a user to interact with a user interface located on receiver. The monitor unit, in some embodiments, may include, e.g., a mobile telephone device, a personal digital assistant, other consumer electronic device such as MP3 device, camera, radio, etc., or other communication-enabled data processing device.

The monitor unit may perform data processing and/or analysis, etc. on the received analyte data to generate information pertaining to the monitored analyte levels. The monitor unit may incorporate a display screen, which can be used, for example, to display measured analyte levels, and/or audio component such as a speaker to audibly provide information to a user, and/or a vibration device to provide tactile feedback to a user. It is also useful for a user of an analyte monitor to be able to see trend indications (including the magnitude and direction of any ongoing trend), and such data may be displayed as well, either numerically, or by a visual indicator, such as an arrow that may vary in visual attributes, such as size, shape, color, animation, or direction. The receiver device may further incorporate an in vitro analyte test strip port and related electronics in order to be able to make discrete (e.g., blood glucose) measurements.

In certain embodiments described herein, on-body unit and monitor unit communicate via communications link (in this embodiment, a wireless RF connection). Communication may occur, e.g., via RF communication, infrared communication, Bluetooth® communication, Zigbee® communication, 802.1x communication, or WiFi communication, etc. In some embodiments, the communication may include an RF frequency of 433 MHz, 13.56 MHz, or the like. In some embodiments, a secondary monitor unit may be provided. A data processing terminal may be provided for providing further processing or review of analyte data.

In certain embodiments, the analyte monitoring system may be a continuous analyte monitor (e.g., a continuous glucose monitoring system or CGM), and accordingly operate in a mode in which the communications via communications link has sufficient range to support a flow of data from the on-body unit to the monitor unit. In some embodiments, the data flow in a CGM system is automatically provided by the on-body unit to the monitor unit. For example, in some embodiments no user intervention is required for the on-body unit to send the data to the monitor unit. In some embodiments, the on-body unit provides the signal relating to analyte level to the receiving unit 300 on a periodic basis. For example, the signal may be provided, e.g., automatically sent, on a fixed schedule, e.g., once every 250 ms, once a second, once a minute, etc. In some embodiments, the signal is provided to the monitor unit upon the occurrence of an event, e.g., a hyperglycemic event or a hypoglycemic event, etc. In some embodiments, on-body unit may further include local memory in which it may record "logged data" or buffered data collected over a period of time and provide the some or all of the accumulated data to monitor unit from time-to-time. A separate data logging unit may be provided to acquire periodically received data from on-body unit. Data transmission may be one-way communication, e.g., the on-body unit provides data to the monitor unit without receiving signals from the monitor unit. In some embodiments, two-way communication is provided between the on-body unit and the monitor unit.

In some embodiments, the analyte monitoring system includes a sensor which obtains an analyte signal which is provided to the monitor unit "on demand." According to such embodiments, the monitor unit requests a signal from the on-body unit, or the on-body unit may be activated to send signal upon activation to do so. Accordingly, one or both of the on-body unit and monitor unit may include a switch activatable by a user or activated upon some other action or event, the activation of which causes analyte-related signal to be transferred from the on-body unit to the monitor unit. For example, the monitor unit is placed in close proximity with a transmitter device and initiates a data transfer, either over a wired connection, or wirelessly by various means, including, for example various RF-carried encodings and protocols and IR links.

In some embodiments, the signal relating to analyte level is instantaneously generated by the analyte sensor upon receipt of the request, and provided to the monitor unit as requested, and/or the signal relating to analyte level is periodically obtained, e.g., once every 250 ms, once a second, once a minute, etc. Upon receipt of the "on demand" request at the on-body unit, an analyte signal is provided to the monitor unit. In some cases, the signal provided to the monitor unit is or at least includes the most recent analyte signal(s).

In further embodiments, additional data is provided to the monitor unit "on demand." For example, analyte trend data may be provided. Such trend data may include two or more analyte data points to indicate that analyte levels are rising, falling, or stable. Analyte trend data may include data from longer periods of time, such as, e.g., several minutes, several hours, several days, or several weeks.

In some embodiments, analyte monitoring systems may further include medication infusion devices integrated therewith. Examples of such embodiments can be found in, among others, U.S. patent application Ser. No. 11/552,065, now U.S. Pat. No. 9,259,175, and Ser. No. 12/032,593, now U.S. Pat. No. 9,636,450, the disclosures of each of which are incorporated herein by reference for all purposes.

Further embodiments of analyte monitoring systems and on demand analyte monitoring system are further disclosed in U.S. Pat. No. 6,175,752 and U.S. Publication Nos. 2011/0213225, 2010/0198034, 2010/0324392, 2011/0319729, 2011/0288574, 2012/0010642 and 2013/0150691, the disclosures of each of which are incorporated herein by reference for all purposes. Further details regarding on demand systems are also disclosed in U.S. Pat. No. 7,620,438, U.S. Patent Publication Nos. 2009/0054749, 2007/0149873, 2008/0064937, 2008/0071157, 2008/0071158, 2009/0281406, 2008/0058625, 2009/0294277, 2008/0319295, 2008/0319296, 2009/0257911, 2008/0179187, 2007/0149875, 2009/0018425, and U.S. patent application Ser. No. 12/625,524, now U.S. Pat. No. 8,390,455, Ser. No. 12/625,525, now U.S. Pat. No. 8,358,210, Ser. No. 12/625,528, now U.S. Pat. No. 8,115,635, Ser. Nos. 12/628,201, 12/628,177, 12/628,198, 12/628,203, 12/628,210, 12/393,921, 61/149,639, 12/495,709, 61/155,889, 61/155,891, 61/155,893, 61/165,499, 61/227,967, 61/163,006, 12/495,730, 12/495,712, now U.S. Pat. No. 8,437,827, 61/238,461, 61/256,925, 61/238,494, 61/238,159, 61/238,483, 61/238,581, 61/247,508, 61/247,516, 61/247,514, 61/247,519, 61/249,535, 12/544,061, 12/625,185, now U.S. Pat. No. 8,354,013, Ser. No. 12/625,208, now U.S. Pat. No. 9,042,954, Ser. Nos. 12/624,767, 12/242,780, now U.S. Pat. No. 8,983,568, Ser. Nos. 12/183,602, 12/211,014, now U.S. Pat. No. 8,636,884, and Ser. No. 12/114,359, now U.S. Pat. No. 8,080,385, the disclosures of each of which are incorporated by reference in their entirety herein for all purposes.

B. Sensor

The sensor, in accordance with one embodiment of the present disclosure, can be configured to detect and monitor an analyte of interest present in a biological sample of a user. The biological sample can be a biological fluid containing the analyte of interest, such as (but not limited to) interstitial fluid, blood, and urine. The analyte of interest can be one or more analytes including acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. However, other suitable analytes can also be monitored, as would be known in the art. Furthermore, the analyte monitoring system can be configured to monitor the concentration of drugs, such as, for example, antibiotics (e.g., gentamicin, vancomycin, and the like), digitoxin, digoxin, theophylline, warfarin, and the like.

During use, the sensor is physically positioned in or on the body of a user whose analyte level is being monitored by an insertion device. The sensor can be configured to continuously sample the analyte level of the user and convert the sampled analyte level into a corresponding data signal for transmission by the transmitter. In some embodiments, the sensor is implantable into a subject's body for a period of time (e.g., three days, five days, seven days, etc.) to contact and monitor an analyte present in the biological fluid. Thus, a new sensor must be used typically every three to seven days.

Generally, the sensor comprises a substrate, one or more electrodes, a sensing layer and a barrier layer, as described below and disclosed in U.S. Pat. Nos. 6,284,478 and 6,990,366, the disclosures of which are incorporated by reference in their entirety herein for all purposes. In one embodiment, the sensor includes a substrate. In some embodiments, the substrate is formed from a relatively flexible material. Suitable materials for a flexible substrate include, for example, non-conducting plastic or polymeric materials and other non-conducting, flexible, deformable materials. Suitable plastic or polymeric materials include thermoplastics such as polycarbonates, polyesters (e.g., Mylar® and polyethylene terephthalate (PET)), polyvinyl chloride (PVC), polyurethanes, polyethers, polyamides, polyimides, or copolymers of these thermoplastics, such as PETG (glycol-modified polyethylene terephthalate). In other embodiments, the sensor includes a relatively rigid substrate. Suitable examples of rigid materials that may be used to form the substrate include poorly conducting ceramics, such as aluminum oxide and silicon dioxide. Further, the substrate can be formed from an insulating material. Suitable insulating materials include polyurethane, Teflon (fluorinated polymers), polyethyleneterephthalate (PET, Dacron) or polyimide.

The substrate can include a distal end and a proximal end. In some embodiments, the distal and proximal ends have different widths. In some embodiments, the distal and proximal ends have the same width. In some embodiments, the proximal end of the sensor remains above the skin surface. In such embodiments, the distal end of the substrate may have a relatively narrow width. Moreover, sensors intended to be positioned at least partially into the tissue of a user's body at can be configured to have narrow distal end or distal point to facilitate the insertion of the sensor. For example, for insertable sensors designed for continuous or periodic monitoring of the analyte during normal activities of the patient, a distal end of the sensor which is to be implanted into the user has a width of 2 mm or less, preferably 1 mm or less, and more preferably 0.5 mm or less. In certain embodiments, as disclosed in U.S. patent application Ser. No. 12/870,818, the disclosure of which is incorporated herein by reference, the sensor substrate distal end is constructed of material and shape to facilitate insertion of the distal end of the sensor through the skin of a patient without the use of an introducer sharp.

A plurality of electrodes can be disposed near the distal end of sensor. The electrodes include working electrode, counter electrode and reference electrode. Other embodiments, however, can include a greater or fewer number of electrodes.

Each of the electrodes is formed from conductive material, for example, a non-corroding metal or carbon wire. Suitable conductive materials include, for example, vitreous carbon, graphite, silver, silver-chloride, platinum, palladium, or gold. The conductive material can be applied to the substrate by various techniques including laser ablation, printing, etching, silk-screening, and photolithography. In one embodiment, each of the electrodes is formed from gold by a laser ablation technique. The sensor can include conductive traces extending from electrodes to corresponding, respective contacts to define the sensor electronic circuitry. In one embodiment, an insulating substrate (e.g., dielectric material) and electrodes are arranged in a stacked orientation (i.e., insulating substrate disposed between electrodes). Alternatively, the electrodes can be arranged in a side by side orientation (not shown), as described in U.S. Pat. No. 6,175,752, the disclosure of which is incorporated by reference in its entirety herein for all purposes.

The sensor can include a sensing material having one or more components designed to facilitate the electrolysis of the analyte of interest. The components, for example, may be immobilized on the working electrode. Alternatively, the components of the sensing layer may be immobilized within or between one or more membranes or films disposed over the working electrode or the components may be immobilized in a polymeric or sol-gel matrix. Further aspects of the sensor are described in U.S. Pat. Nos. 5,262,035, 5,264,104, 5,264,105, 5,320,725, 5,593,852, and 5,665,222, each of which is incorporated by reference in its entirety herein for all purposes.

In some embodiments, the sensor is a self-powered analyte sensor, which is capable of spontaneously passing a currently directly proportional to analyte concentration in the absence of an external power source. Any exemplary sensor is described in U.S. patent application Ser. No. 12/393,921, filed Feb. 26, 2009, which is hereby incorporated by reference in its entirety herein for all purposes.

C. Inserter

In one aspect of the present disclosure, an inserter is provided. The object to be inserted into the subject can be, for example, an analyte sensor as described above. Alternatively, other objects such as but not limited to an infusion set, or lancing device can be inserted.

An exemplary embodiment of the sensor inserter assembly 100 is illustrated in FIGS. 1-5. Generally, the sensor inserter assembly 100 includes a sensor (not shown) preloaded within inserter 110. After preparing an insertion site on the skin of a user, the user removes an upper liner 116 and lower liner 118 from an adhesive mount 112 to expose the bottom surface and a portion of the top surface of an adhesive tape located on the bottom surface of the mount 112. Mount 112, with inserter 110 attached, is then applied to the user's skin at the insertion site. The inserter includes an actuator button 124 to be pressed causing inserter 110 to fire, thereby inserting sensor 114 (not shown in FIG. 1) into the user's skin S. In some embodiments of the present disclosure, the inserter 110 includes a safety member to impede actuation of the inserter as described below. Mount 112, in certain embodiments, may be configured to receive inserter 110 in only a single configuration, thus ensuring proper alignment of the inserter 110 on the mount. Exemplary embodiments of mount and inserter configured for proper alignment can be found in, among others, U.S. patent application Ser. No. 11/380,883, and Ser. No. 11/535,983, now U.S. Pat. No. 7,697,967, the disclosures of each of which are incorporated herein by reference for all purposes.

Once sensor 114 has been inserted into the skin S, the user removes inserter 110 from mount 112 by pressing release tabs 126 on opposite sides of inserter 110 and lifting inserter 110 away from mount 112. Further details of the inserter assembly 100 are provided in U.S. Pat. No. 7,381,184, which is incorporated by reference in its entirety herein for all purposes. In other embodiments, the inserter maybe integrated with the mount, wherein after insertion of the sensor through the skin of the patient, the sensor electronics unit is slid into place on the mount, while the inserter remains part of the mount. Exemplary embodiments are disclosed in, among others, U.S. patent application Ser. No. 11/216,932, now U.S. Pat. No. 7,731,657, Ser. Nos. 11/192, 773, 11/240,257, now U.S. Pat. No. 7,883,464, Ser. No. 11/240,259, now U.S. Pat. No. 8,512,243, and Ser. No. 11/530,472, now U.S. Pat. No. 8,333,714, the disclosures of each of which are incorporated herein by reference for all purposes.

Figure 3:
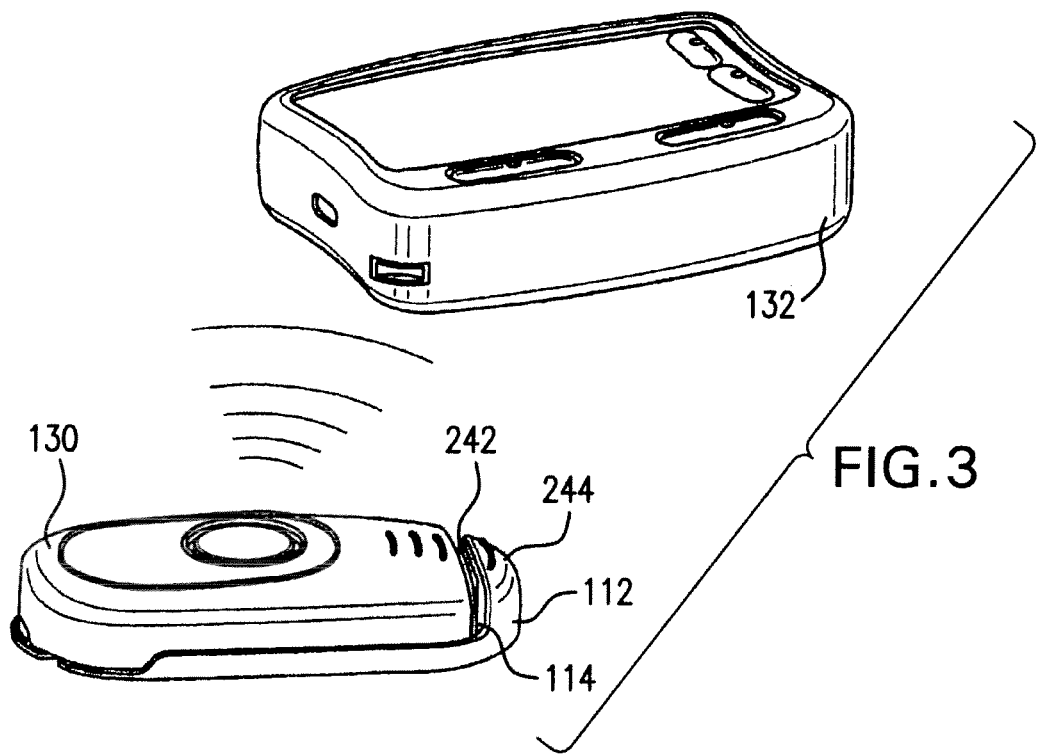
FIG. 3 is a perspective view of the transmitter attached to the adhesive mount in accordance with the disclosed subject matter.

Once inserter 110 is removed from mount 112, sensor electronics unit 130 can be slid into place, as illustrated in FIG. 3. The circuitry of sensor electronics unit 130 makes electrical contact with the contacts on sensor 114 after sensor electronics unit 130 is fully seated on mount 112. As discussed hereinabove, mount 112, together with sensor 114, and sensor electronics unit 130 comprises an on-body unit. In some embodiments, sensor electronics unit 130 may include communications circuitry, such as a transmitter, transceiver, or the like, for communicating with additional equipment. For example, once initialization and synchronization procedures are completed, electrochemical measurements from sensor 114 can be sent, e.g., wirelessly from sensor electronics unit 130 to a monitor unit, such as portable receiver 132, as shown in FIG. 3. Sensor 114, mount 112 and sensor electronics unit 130 remain in place on the user for a predetermined period, currently envisioned to be several hours, to several days, e.g., about three days, about five days, about seven days, etc. After expiration of the lifetime of the sensor, these components are then removed so that sensor 114 and mount 112 can be properly discarded. The entire procedure above can then be repeated with a new inserter 110, sensor 114 and mount 112. In some embodiments, the sensor electronics unit 130 and receiver 132 are durable and are reused.

Figure 4:
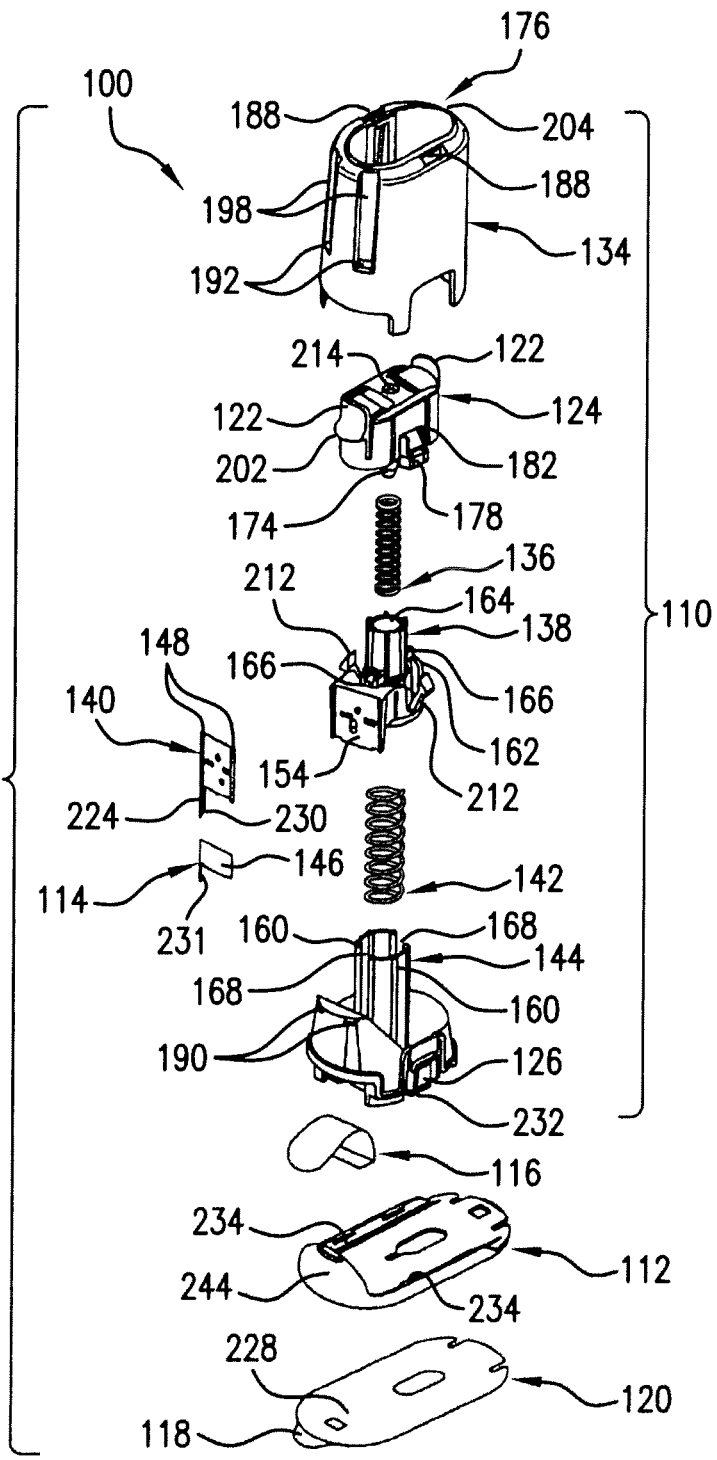
FIG. 4 is an exploded perspective view of the embodiment of FIG. 1.

Referring to FIG. 4, the inserter assembly 100 according to one embodiment can be assembled as shown from the following components: e.g., housing 134, actuator button 124, drive spring 136, shuttle 138, introducer sharp 140, sensor 114, retraction spring 142, inserter base 144, upper liner 116, mounting unit 112, adhesive tape 120, and lower liner 118.

Sensor 114 has a main surface 146 slidably mounted between U-shaped rails 148 of introducer sharp 140. Introducer sharp 140 can be mounted to face 154 of shuttle 138, such as with adhesive, heat stake or ultrasonic weld. U.S. patent application Ser. No. 11/216,932, now U.S. Pat. No. 7,731,657, Ser. No. 11/617,698, now U.S. Pat. No. 8,545,403, and Ser. No. 11/535,983, now U.S. Pat. No. 7,697,967, disclose additional embodiments of sensor introducer sharps and insertion devices, the disclosures of which is incorporated herein by reference.

In some embodiments, shuttle 138 can be slidably and non-rotatably constrained on base 144 by arcuate guides 160. The shuttle can be generally formed by an outer ring 162 and an inner cup-shaped post 164 connected by two bridges 166. Bridges 166 can be configured to slide between the two slots 168 formed between guides 160 and allow shuttle 138 to travel along guides 160 without rotating. Retraction spring 142 can be captivated at its outer circumference by guides 160, at its bottom by the floor 170 (FIG. 5) of base 144, at its top by bridges 166, and at its inner circumference by the outer surface of shuttle post 164. Drive spring 136 is captivated at its bottom and outer circumference by the inside surface of shuttle post 164, at its top by the ceiling 172 (FIG. 5) inside actuator button 124, and at its inner circumference by stem 174 depending from ceiling 172.

When drive spring 136 is compressed between actuator button 124 and shuttle 138 it can urge shuttle 138 towards base 144. When retraction spring 142 is compressed between shuttle 138 and base 144, it urges shuttle 138 towards actuator button 124.

Figure 5:
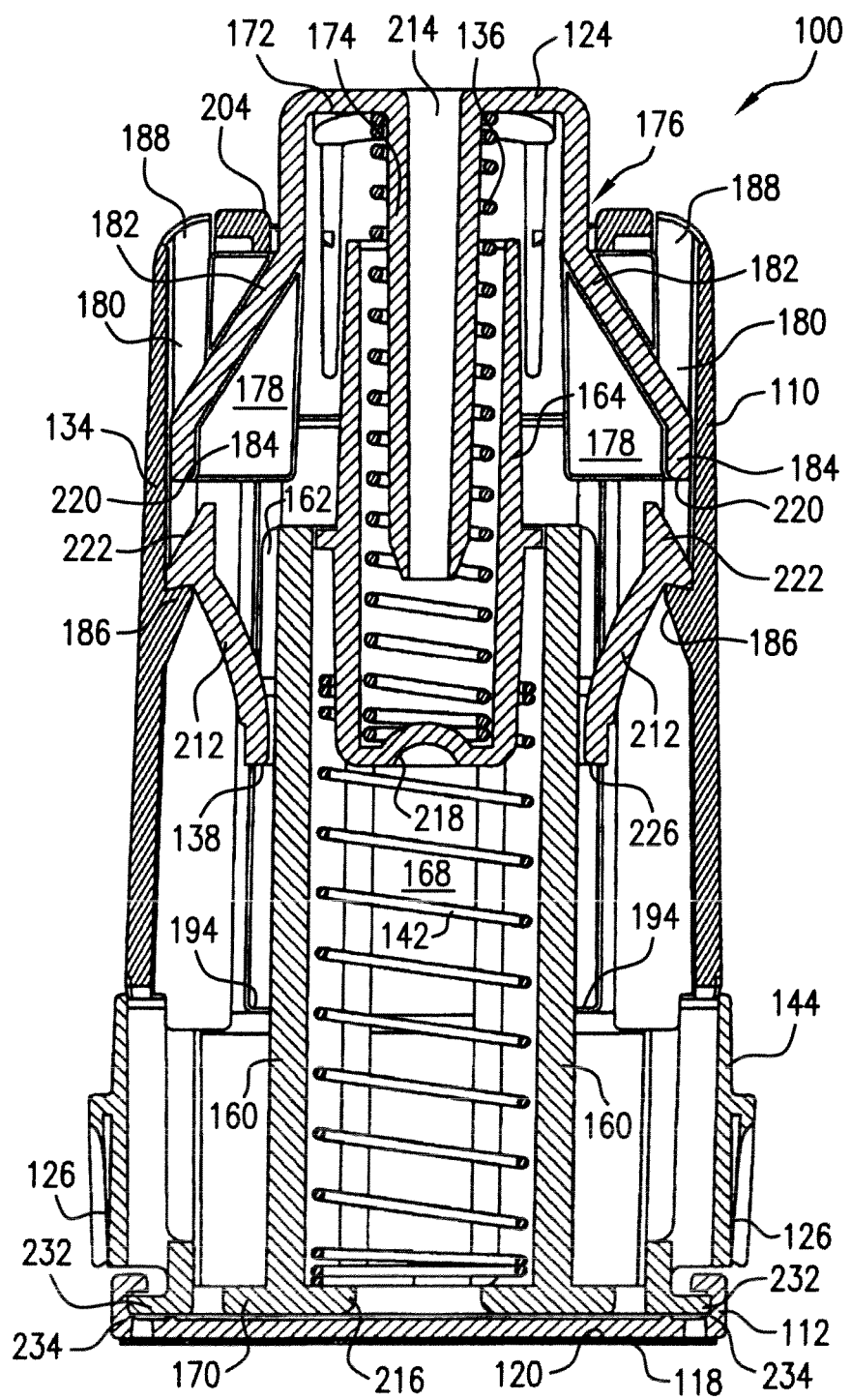
FIG. 5 is a cross-sectional view of the inserter of FIG. 1.

In some embodiments, the actuator button 124 is slidably received within housing 134 from below and resides in opening 176 at the top of housing 134 with limited longitudinal movement. Arms 178 on each side of actuator button 124 can be configured to travel in channels 180 along the inside walls of housing 134, as best seen in FIG. 5. Longitudinal movement of actuator button 124 can be limited in one direction by the base 182 of arms 178 contacting the edge of opening 176 at the top of housing 134, and in the other direction by the distal ends 184 of arms 178 contacting stops 186 in channels 180. Slots 188 are preferably provided in the top of housing 134 for ease of housing manufacture and so tools can be inserted to inwardly compress arms 178 beyond stops 186 to allow actuator button 124 to be removed from housing 134 if needed.

When sensor 114, introducer 140, shuttle 138, retraction spring 142, drive spring 136 and actuator button 124 are assembled between base 144 and housing 134 as shown in FIG. 5 and described above, housing 134 is snapped into place on base 144. Base 144 is held onto housing 134 by upper base barbs 190 that engage upper openings 192 in housing 134, and lower base barbs 194 that engage lower openings 192 in housing 134.

Figure 6:
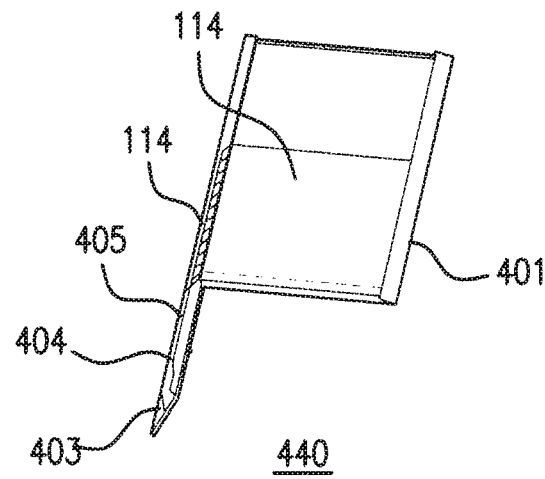
FIG. 6 is a schematic depiction of an introducer and sensor in accordance with the disclosed subject matter.

Generally, in accordance with one embodiment of the present disclosure, as illustrated in FIG. 6, an introducer 440 is provided which comprises a body portion 401 and a shaft portion 405. Introducer 440 is substantially identical to introducer 140, and useful with an inserter, such as inserter assembly 100 described hereinabove, with the differences illustrated in the accompanying figures, and described herein. The shaft portion 405 can include a substantially sharp distal edge segment 403 to contact and pierce the skin of a user for transcutaneous placement of the sensor through the user's skin S. As shown, the sensor 114 is retained within the shaft portion 405 of the introducer 440 and is configured to be held in position during insertion of the sensor through the user's skin by the substantially hollow cylindrical shape of the shaft portion 405, as illustrated in FIG. 6.

Figure 7:
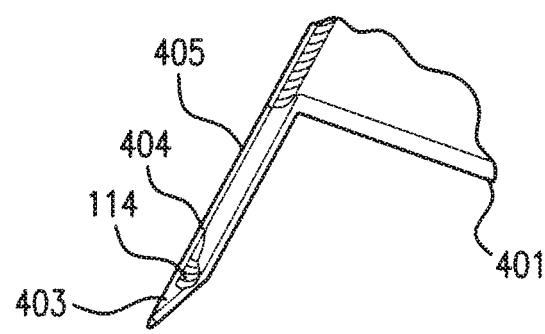
FIG. 7 is a is a schematic depiction of a shaft portion of the introducer in accordance with the disclosed subject matter.

In some embodiments, referring to FIGS. 6 and 7, the tip of the analyte sensor 114 can be retained at the distal edge segment 403 of the introducer 440 during the subcutaneously or transcutaneous positioning of the sensor 114 through the user's skin. Thus, the sensor 114 is positioned within the substantially hollow shaft portion 405 of the introducer 440. The distal edge segment 403 of the introducer 440 is configured to first pierce through the user's skin, and guide sensor retained in the shaft portion 405 of the introducer 440 through the pierced skin of the user. After placement of the sensor 114 at the desired location under the skin, the introducer 440 can be retracted from the user, leaving the sensor 114 in place. In some embodiments, during the introducer removal process, a radial configuration 404 of the shaft portion 405 is configured to guide the removal of the introducer 440 from the pierced skin.

In some embodiments, the shaft portion includes one or more holding members configured to retain the sensor in the introducer. For example, but not limitation, the shaft portion 405 of the introducer 440 may have a ribbed configuration to provide additional friction fit during the insertion of the introducer and sensor through the skin of the user.

Figure 8:
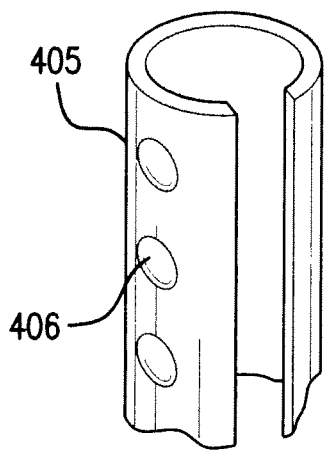
FIG. 8 is a perspective view of a shaft portions having one or more holding member in accordance with the disclosed subject matter.
Figure 9:
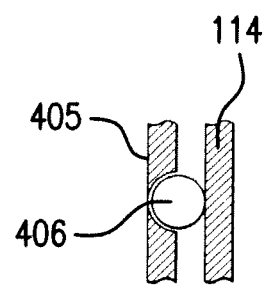
FIG. 9 is a sectional view of the shaft portion of FIG. 8 in accordance with the disclosed subject matter.

The holding member can include various configurations, as depicted in FIGS. 8 to 31. In one embodiment, as shown in FIGS. 8-9, the shaft portion 405 may include one or more rolling members 406. The rolling members 406 can include for example rollers, balls, or wheels. In some embodiments, the rolling members 406 are disposed within the channel or wall of the shaft portion 405. The rolling members 406 are configured to retain the sensor 114 in the introducer 140 by friction forces prior to insertion of the sensor 114 into the user's body. During the insertion process, the rolling members 406 can turn or rotate to displace the sensor 114 from the introducer shaft 405 during the insertion process. When the sensor 114 is placed at the desired depth and caught in the mount as part of the insertion (e.g., by hook, clamp or gripper), the rolling members 406 rotate from the friction from the sensor 114 as the introducer exits back into the inserter.

Figure 10:
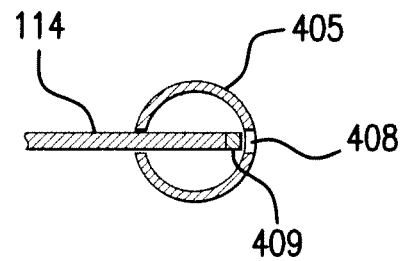
FIG. 10 is a sectional view of a shaft portion having one or more holding member in accordance with the disclosed subject matter.
Figure 11:
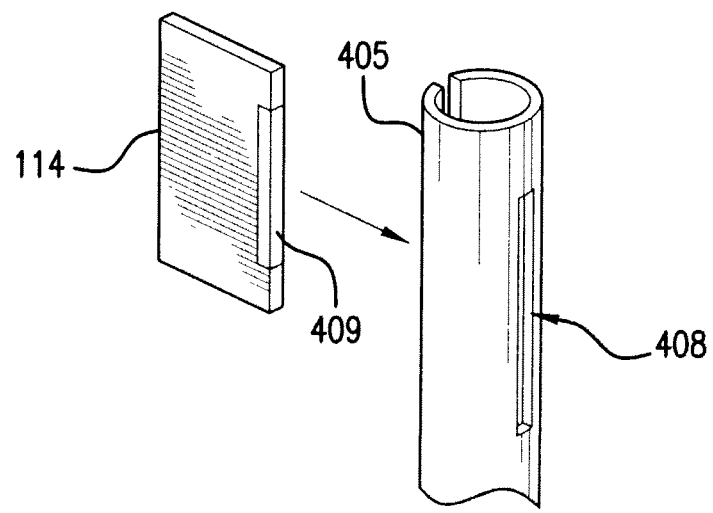
FIG. 11 is a perspective view of the shaft portion of FIG. 10 in accordance with the disclosed subject matter.

In some embodiments, as shown in FIGS. 10-11, the shaft portion 405 of the introducer 140 and the sensor 114 comprise a magnet 408 or magnetized area 409, such that magnetic forces retain the sensor within the introducer. The magnetic material can be any material that will provide magnetic forces including, but not limited to, low grade stainless steel, carbon ink, and the like. In some embodiments, the shaft or the sensor can be doped with magnetic metal. The magnet can be disposed along the channel of the shaft portion. In this regard, in accordance with one embodiment, magnetic material can be embedded on the surface of the sensor. Further, a magnet or a magnetized area is fit into the sharp to hold the sensor in place. Release of the magnetic force can occur when the shaft portion 405 is removed as part of the insertion process of the sensor delivery unit.

In other embodiments, as illustrated in FIG. 12, the holding member comprises a sheath 407 disposed coaxially about the shaft portion 405. The sheath 407 can comprise one or more perforations along a perforation line 410 disposed along a length of the sheath. In this manner, the sheath can be a tear away member. In some embodiments, the sheath comprises a polymer film. The polymer film can be attached to an outer surface of the shaft portion. Suitable materials for the sheath include polyimide, Pebax, polyethylene, Nylon, PTFE, polyester, and polyurethane.

In another embodiment, as depicted in FIGS. 13-14, the shaft portion 405 can include one or more windings 411 configured to releasably retain the sensor 114. The windings are generally a wound member 411 having the capability to unwind, as illustrated in FIG. 14. While the winding 411 is in the wound configuration, it applies an interference against the sensor body to retain the sensor 114. The sensor can be displaced from the shaft portion 405 upon unwinding the one or more windings. In some embodiments, the windings comprise wound rolls of polymer film.

Figure 15:
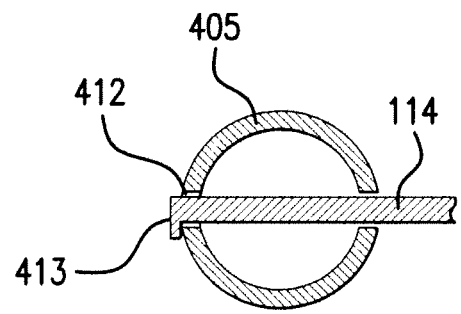
FIG. 15 is a sectional view of a shaft portion having one or more holding member in accordance with the disclosed subject matter in a second configuration.
Figures 16, 17:
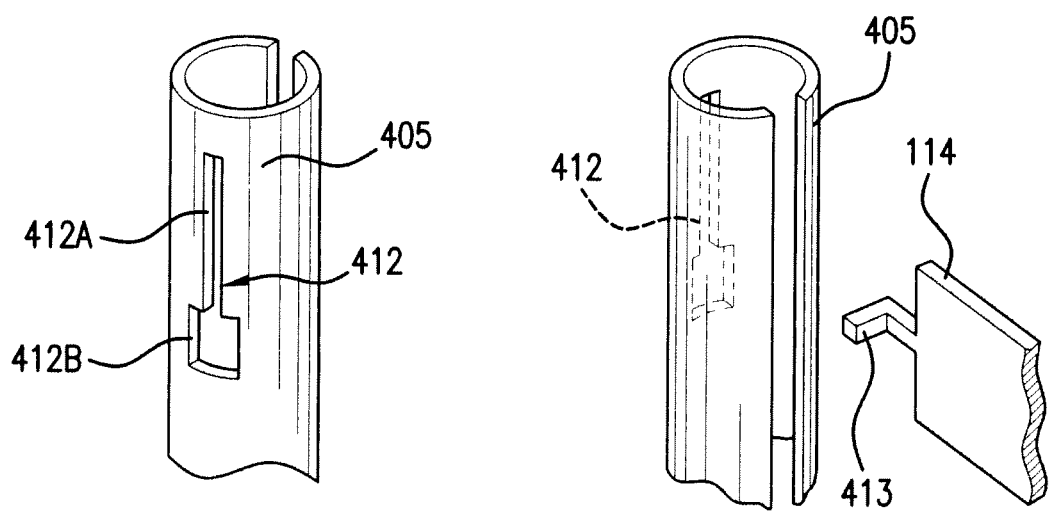
FIG. 16 is a perspective view of the shaft portion of FIG. 15 in accordance with the disclosed subject matter.
FIG. 17 is a perspective view of the shaft portion of FIG. 15 in accordance with the disclosed subject matter.

In other embodiments, the shaft portion 405 of the introducer 140 includes a substantially longitudinal opening 412, as shown in FIGS. 15-17. The sensor 114 can include a flange 413 disposed along an edge of the sensor body 114 to communicate through the longitudinal opening 412. The engagement of the longitudinal opening 412 and the flange 413 provide an interference fit to retain the sensor 114. In some embodiments, the slot includes a distal section 412B configured to be wider than the width of a proximal section 412A, and sufficiently wide such that the sensor flange 413 may be displaced from the shaft when the flange becomes disposed in the wider section of the opening 412, for example during the insertion process as the sensor travels towards an insertion position. In this manner, the longitudinal opening 412 can be provided with a greater width at a distal section to allow the introducer 140 to be completely de-coupled from the sensor 114 retained within the shaft portion 405 during the placement thereof, so that the introducer 140 may be removed completely from the user, while leaving in place the sensor 114.

Figure 18:
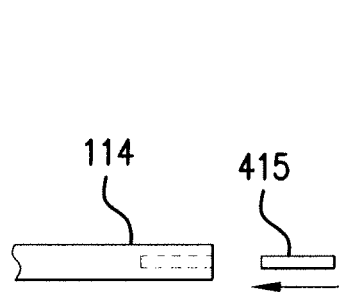
FIGS. 18-20 are views of a shaft portion in accordance with the disclosed subject matter.
Figure 19:
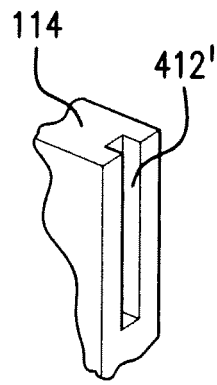
Figure 20:
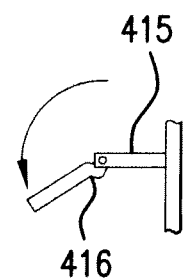

As an alternative, illustrated in FIGS. 18-20 the sensor 114 can be configured to include a pin 415 extending from a lateral end of the sensor body. Similar to the flange member described above, the pin can engage a slot 412' formed in the introducer so as to retain the sensor in the introducer. In some embodiments, the pin can be configured as a hinge member 416.

Figure 21:
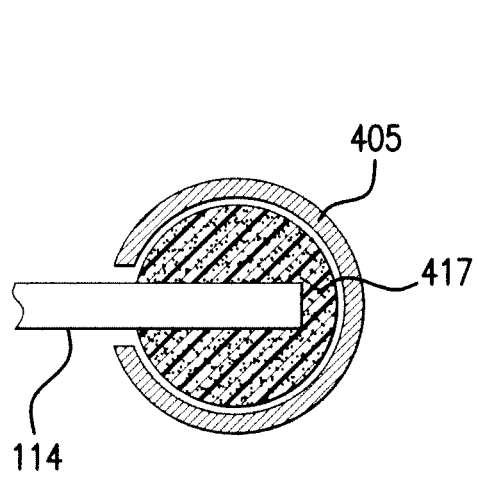
FIG. 21 is a sectional view of a shaft portion having one or more holding member in accordance with the disclosed subject matter in a second configuration.

In yet another embodiment, the holding member can include a sponge material 417 disposed along the channel of the shaft portion 405, as shown in FIG. 21. The sponge material 417 can be configured to provide a soft interference fit with a sensor 114 disposed in the shaft portion 405 and may comprise polyurethane, polyether, polystyrene, or isoprene foams. The foams can be attached via adhesive, or applied during the lubricious coating process (i.e., a silicone coating used to reduce friction and make insertion more smooth).

Figure 22:
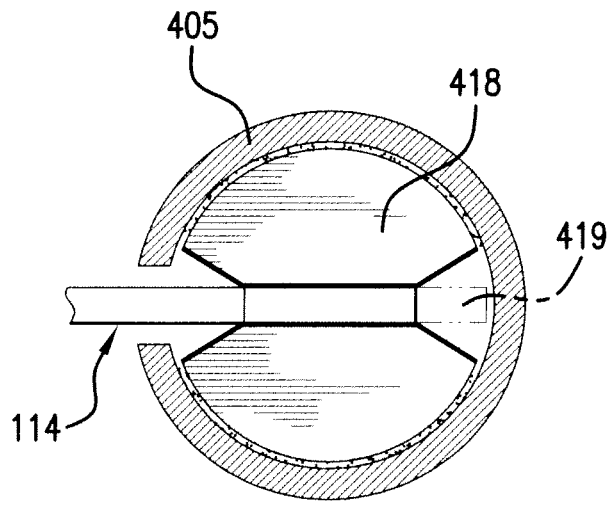
FIG. 22 is a sectional view of a shaft portion having one or more holding member in accordance with the disclosed subject matter in a second configuration.

In other embodiments, the shaft 405 is provided with a diaphragm 418, such as a thin, semi-rigid membrane housed along a portion of the channel. The diaphragm can include an opening 419 to receive and retain the sensor, as shown in FIG. 22. The diaphragm 418 may be molded or cast polymer (silicone, urethane or TPE) plug or insert with a series of slits or webbing similar to an iris. Or it could be a type of a duckbill valve. In one embodiment, the diaphragm 418 is fixed (molded or glued) to the inner diameter of the introducer. The diaphragm 418 may be rigid enough to hold the sensor but flexible to open when the senor is captured during insertion.

In another aspect of the present disclosure, the introducer 440 may be configured to reduce the insertion and extraction forces through the user's skin, thus reducing trauma to the skin. In this regard, the introducer 440 can be configured to include a compressible member 518 attached to a lateral side of the introducer 440, as illustrated in FIGS. 23-24. In some embodiments, the compressible member 518 can include a first section, or barrel 519, and a second section, or plunger 520, as shown in FIG. 23. The first section 519 can include a compressible body. For example, the compressible body can include a spring, such as a compression spring 522 (illustrated in dashed lines). In some embodiments, the first section 519 includes a housing comprising the spring. The springs may be helical compression springs having variable pitch and compression rate. The shape of the spring can be straight, hourglass, conical or barrel. Alternatively, a controlled friction can be used to allow a plunger 520 to move inside the barrel 519 at a set force. When the predetermined "break force" is reached, the plunger 520 can move. As illustrated in FIGS. 26-27, the shaft 405 of the introducer 440 is attached in some embodiments to the housing of the compression member 518.

In some embodiments, the second section 520 of the compressible member 518 is non-compressible, but retractable. For example, the second section 520 can be formed from a solid thermoplastic member. The first section 519 can be configured to receive the second section 520. In this manner, the compressible member 518 can be compressed upon retraction of the second section 520 within the first portion housing 519. In this regard, the first and second sections can have a telescoping relationship, such that the sliding engagement of the second member upwardly into the first member causes compression of the compressible member, as illustrated in FIG. 25. A first position of second section 520 is illustrated in dashed line and the second position of the second section 520 is illustrated in solid line.

The compression of the compressible member 518 by the retraction of the second member 520 causes the distal edge 403 of the introducer shaft, i.e., the sharp, to contact and pierce through the skin of the user.

Figure 30:
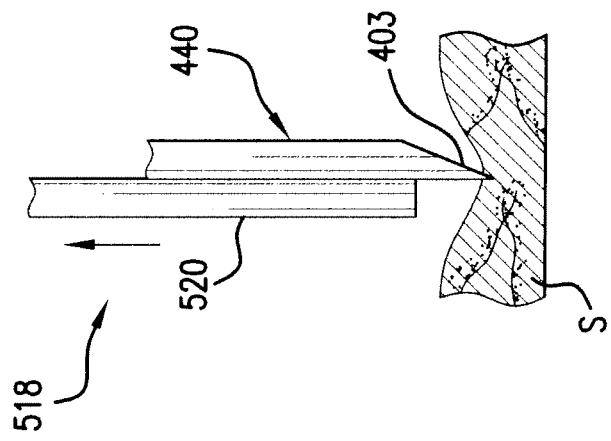
FIG. 28-30 are schematic depictions of the introducer of FIGS. 23-27 depressing the skin and retracting to allow introducer sharp to pierce the skin in accordance with the disclosed subject matter.
Figure 29:
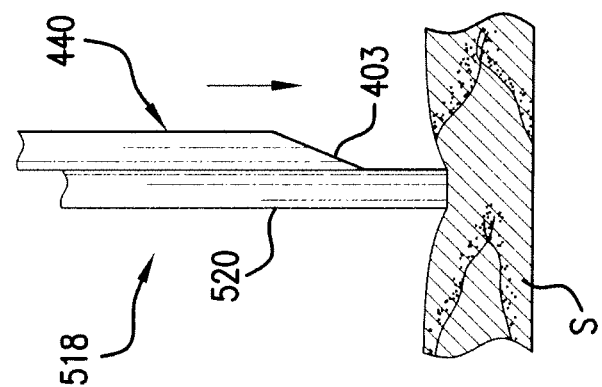
Figure 28:
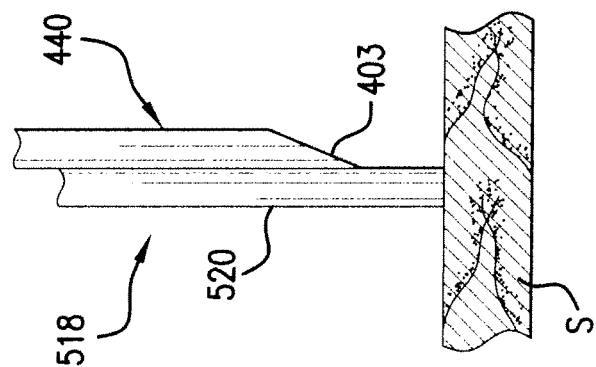

During operation, as shown in FIGS. 28-30, the compressible member 518 contacts the skin S of a user. During this process, the second section 520 of the compressible member contacts the skin S prior to the introducer edge 403 because the distal end of the compressible member 518 is initially distal to the introducer distal end 403. See FIGS. 28-29. In this manner, the second member 520 can depress the skin S from the pressure of the contact between the second section 520 and the skin S. As shown in FIG. 30, the distal end 403 of the introducer 440 then makes contact with the skin S, as the compressible section 518 compressed upon retraction of the second section 520 upwardly to allow the distal end 403 of the introducer 440 to puncture the skin S and proceed to insert the sensor 114 (not shown in FIG. 30). The compressible member 518 allows control of the depth of the puncture. By maintaining a relatively small skin puncture, it is possible to reduce the amount of potential bleeding during the skin piercing process for subcutaneous or transcutaneous sensor placement, and likewise the result is less bruising and also faster healing.

In some embodiments, the edge segment 403 of the introducer 440 guides the sensor 114 into and through the skin puncture. The edge segment 403 may be sharpened and polished to facilitate a smooth puncture and a clean cut through the user's skin. In this regard, the substantially hollow shaft portion can be configured to minimize the necessary force to deploy the introducer, and minimize pain and skin trauma during puncture and removal of the introducer from the skin. In this regard, the edge segment 403 of the introducer 440 includes a substantially sharp and angled tip (as shown in FIG. 6) for piercing the user's skin. The edge segment 403 of the introducer 440 can be sharp and tapered to facilitate skin piercing while minimizing skin trauma. In this manner, it is possible to minimize the size of the skin wound at the piercing site where the introducer 440 is placed through the skin, and thus, the user will likely experience a faster healing time.

Referring to FIGS. 31-45, actuator 124 described hereinabove can be provided with a safety member, such as safety member 625, 625', 625", 634, 636, 650, configured to impede actuation of the actuator, by for example, preventing the actuator button 124 from being depressed. Accordingly, the safety member can avoid accidental firing of inserter assembly 100. The safety member can take the form of various configurations.

Figure 31:
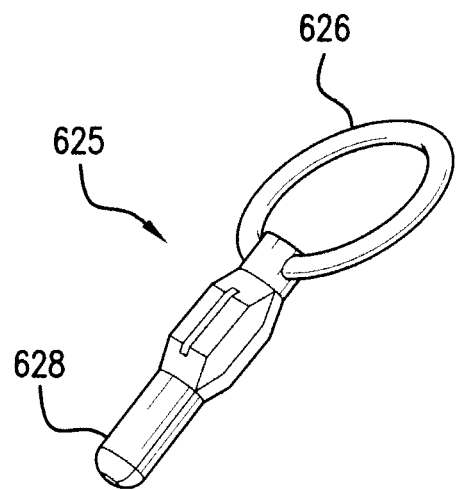
FIGS. 31-45 are perspective views of some embodiments of the safety member of the sensor inserter assembly in accordance with the disclosed subject matter.
Figure 32:
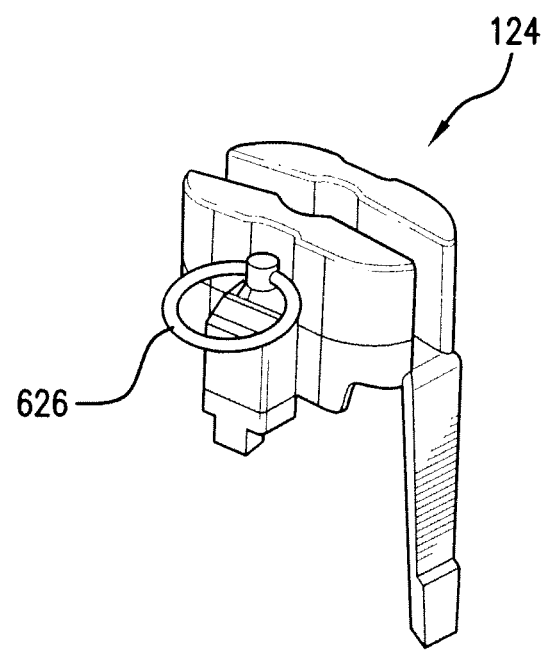
Figure 33:
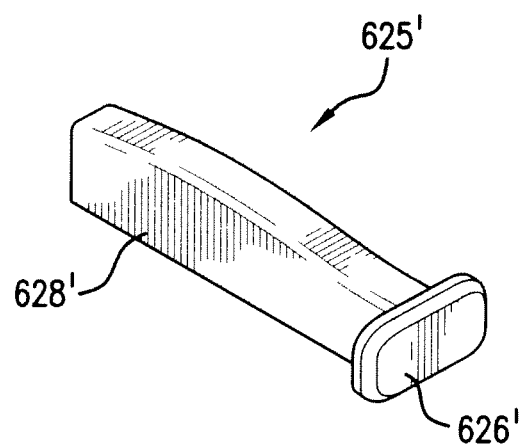
Figure 34:
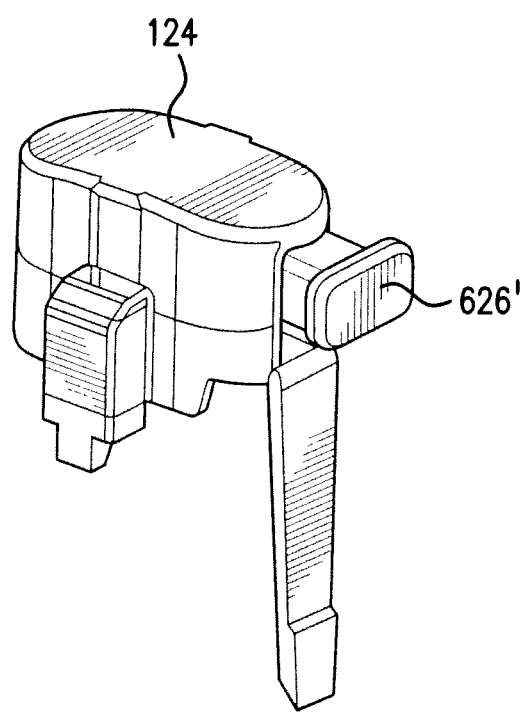

For example, the safety member 625 can comprise a pin or a plug member, such as, but not limited to, a "grenade" pin, or molded plug, as disclosed in FIGS. 31-36. In this regard, as depicted in FIGS. 31-32, the actuator 124 can include one or more apertures or slots (not shown) extending through the actuator 124 through which the safety pin 628 is disposed. The safety member can further include a pull tab 626 for ease of removal to deactivate the safety. As depicted in FIGS. 33-34, the actuator 124 can include one or more apertures or slots (not shown) extending through the actuator 124 through which the safety pin 628' is disposed. The safety member can further include a pull tab 626' for ease of removal to deactivate the safety.

Figure 35:
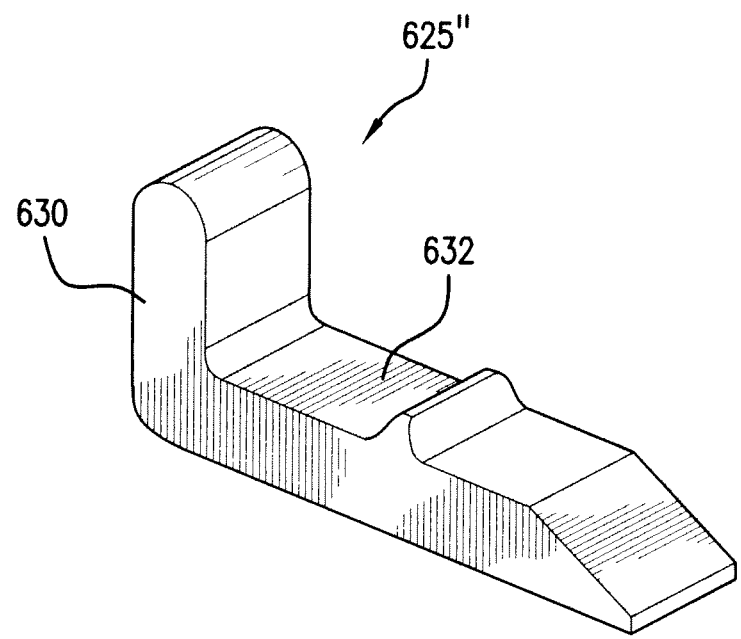
Figure 36:
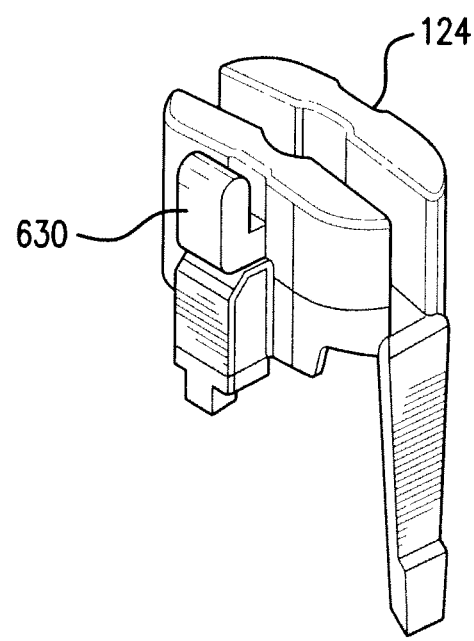

In yet another embodiment, the safety member 625" can include a body having a first end 630 and a second end 632 configured to form an L-shaped body, as shown in FIGS. 35-36. In this regard, the L-shaped safety member includes, as part of its unitary body a pull tab 630 that protrudes from the slot or aperture formed in actuator 124. In this manner, the first or second ends of the L-shaped body can define a pull tab for deactivation of the safety.

Figure 37:
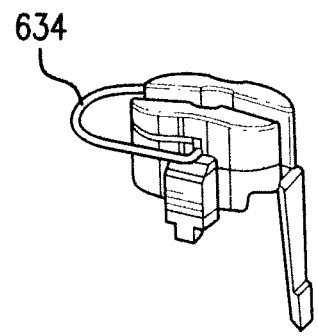
Figure 38:
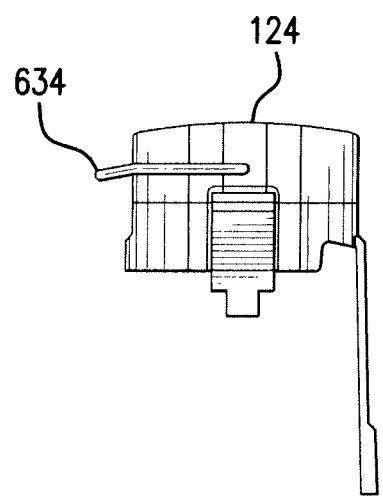
Figure 39:
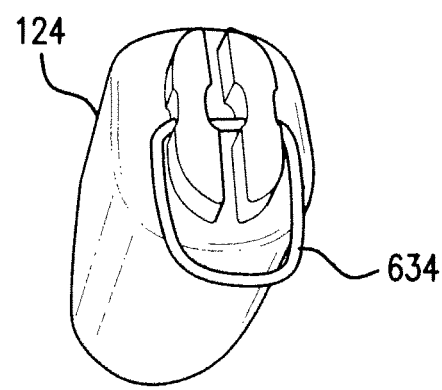

In other embodiments, the safety member comprises a D-ring 634, as shown in FIGS. 37-38. The D ring 634 can be formed from plastic or a metal. As illustrated in FIG. 39, the actuator can include a slot having an opening in communication with the exterior of the actuator. The D-ring can be slid and disposed in the slot, as shown in FIG. 38.

Figures 40, 41:
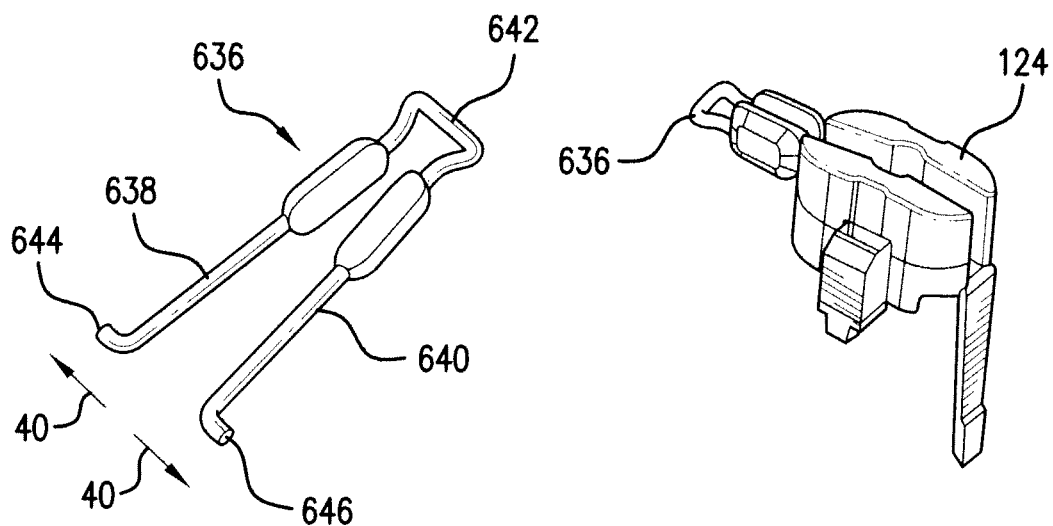
Figure 42:
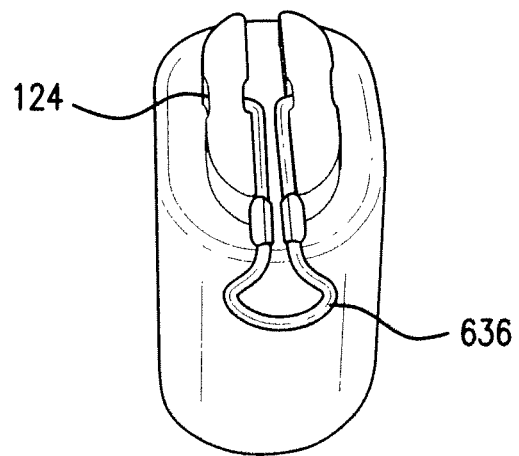

In yet another embodiment, the safety member can comprise a press clip 636, as illustrated in FIGS. 40-42. The press clip 636, in some embodiments, comprises first and second legs 638, 640 connected to each other at a bridging member 642. The press clip 636 includes first and second feet 644, 646 configured to be disposed in one or more apertures formed in the actuator, as illustrated in FIGS. 41 and 42. The configuration of clip 636 provides an outward force, as indicated by arrows 40. The press clip 646 can be disposed in one or more apertures formed on an interior surface of the actuator 124 as illustrated in FIG. 42.

Figure 43:
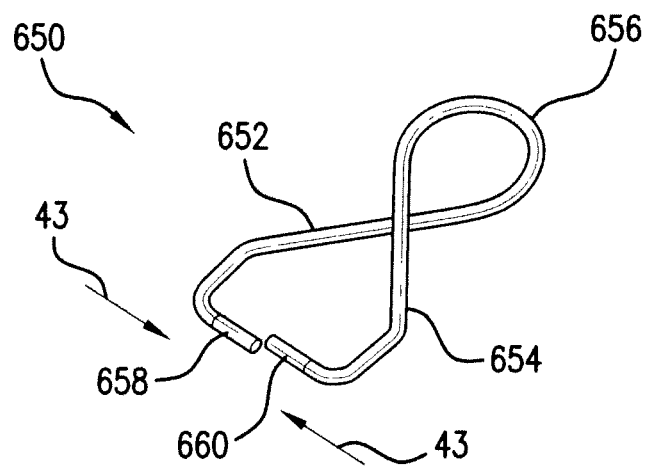
Figure 44:
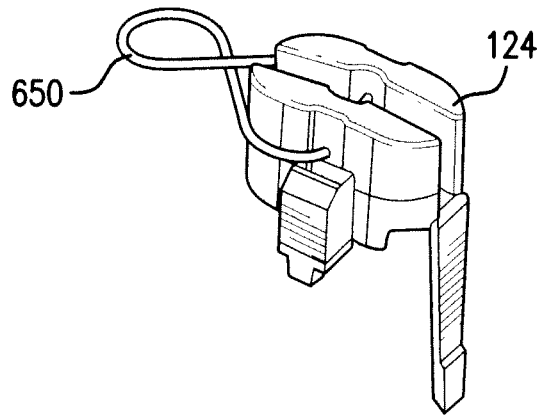
Figure 45:
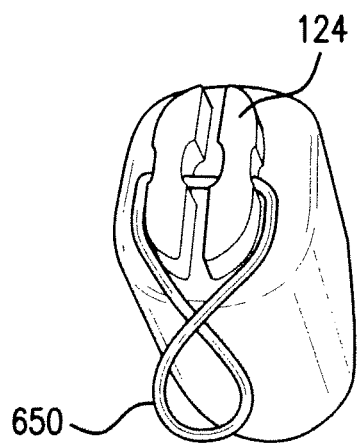

In yet another embodiment, the safety member can comprise a press clip 650, as illustrated in FIGS. 43-45. The press clip 650, in some embodiments, comprises first and second legs 652, 654 connected to each other at a bridging member 656. The press clip 650 includes first and second feet 658, 660 configured to be disposed in one or more apertures formed in the actuator 124, as illustrated in FIGS. 44 and 45. The configuration of clip 650 provides an inward force, as indicated by arrows 43. The press clip 650 can be disposed in one or more apertures formed on an exterior surface of the actuator 124 as illustrated in FIG. 45.

During disposition of the safety member 625 in the actuator, depression of the actuator is impeded. The safety member can be formed from a variety of materials. For example, the material can be a thermoplastic material, such as TPE materials or a metal. In some embodiments, the thermoplastic material has a shore hardness of about 40 to 50. In another embodiment, plastic, metal, wood, or paper can be formed in the shape of a pin as long as it could serve to prevent the downward movement of the button.

Upon deactivation of the safety member such as by removal of the safety member, tabs 122, as illustrated in FIGS. 1 and 5, can be squeezed inward just enough to clear the rim 204 of opening 176 while pressing the actuator button 124 down to fire the inserter. Alternatively, tabs 122 can be squeezed further inward so that barbs on the inside edges can engage catches located on a center portion of actuator button 124 by simply pressing down on the actuator button 124.

Referring back to FIG. 5, shuttle 138 is provided with laterally extending barbed fingers 212 which travel in channels 180 along the inside walls of housing 134. When shuttle 138 is inserted up into housing 134 far enough, barbed fingers 212 momentarily deflect inward and then snap outward again to catch on stops 186. In this armed or cocked position as shown, drive spring 136 is compressed and urging shuttle 138 towards base 144, but barbed fingers 212 catching on stops 186 prevent such travel.

Figure 46:
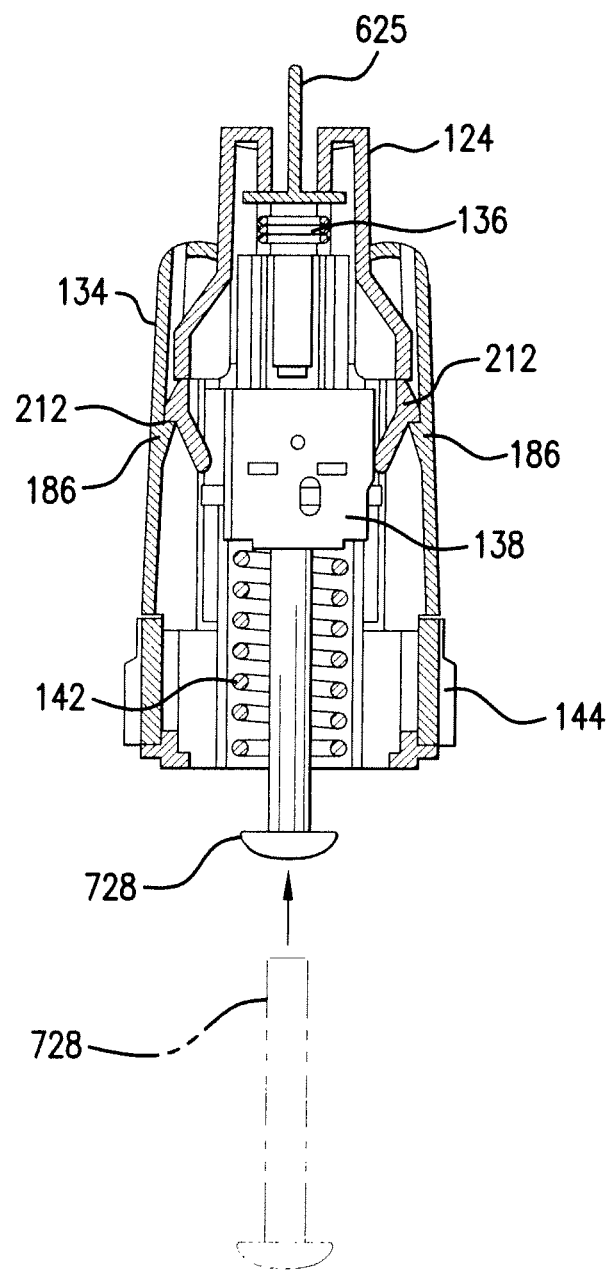
FIG. 46 is a cross-sectional view of an inserter having a pin disposed against the shuttle of the inserter in accordance with the disclosed subject matter.
Figure 47:
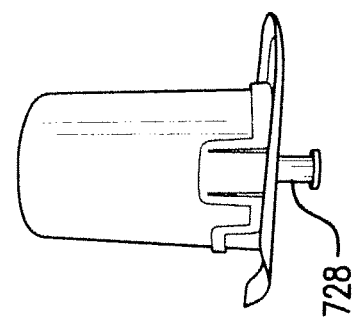

After manufacture of the sensor inserter assembly, the sensor inserter assembly can be shipped in an unarmed position. In this manner, no safety member as described above is necessary for safe shipping or handling as the sensor inserter assembly in its unarmed position cannot fire. In this regard, as shown in FIG. 46 the sensor inserter assembly 110 in its unarmed position can include a pin 728 member, such as a plastic tubular member, disposed in the firing path of the inserter. The pin 728 is configured to butt against the bottom of the shuttle 138 and protrude from the bottom surface of the sensor inserter assembly, as shown in FIGS. 46 and 47. The pin 728 can keep the shuttle from bouncing on the return spring.

Figure 49:
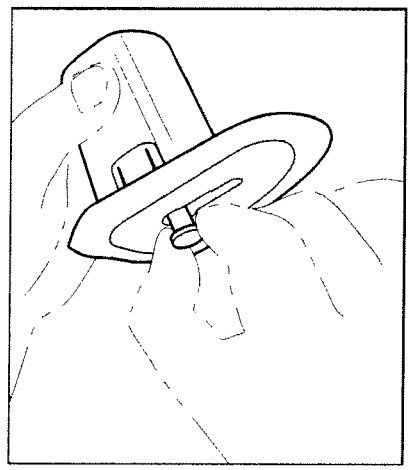
FIGS. 47-49 illustrate a method of arming a sensor.
Figure 48:
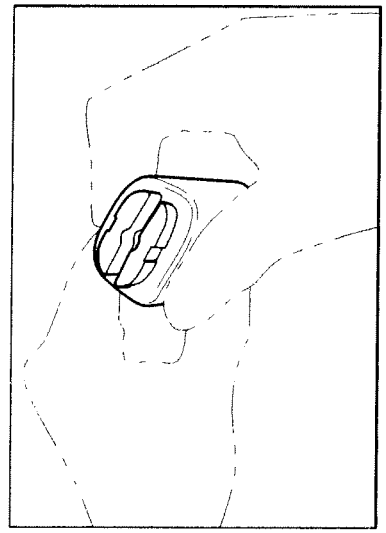

In another aspect of the present disclosure, a method is provided to arm the sensor inserter assembly. The sensor can be armed by the user prior to insertion of a sensor. The method includes, as shown in FIGS. 47-49, contacting the sensor inserter assembly against a surface, such as a table top. The contact of the pin 728 with a relatively hard surface causes the pin to be pushed upwardly the retraction position such that the barbed fingers 212 are moved to a cocked position, as described above. In this manner, the sensor inserter assembly can be configured such that an audible click is sounded when the barbed fingers move to position. During movement to the armed position, the actuator button 124 moves upwardly to the cocked position. After the barbed fingers and the actuator are armed, the pin 728 is removed from the sensor insertion assembly and the sensor inserter assembly is armed and ready to use.

In operation, the user arms the drive mechanism, such as the first spring, to generate the sufficient inertial force needed to drive the introducer and the sensor through the user's skin. In one embodiment, the introducer and the sensor are provided in a fully assembled sensor inserter assembly package within a transmitter mounting unit. Thus, when the user wishes to place the sensor subcutaneously or transcutaneously, the drive mechanism is armed, and the user places the transmitter mount on the surface of the user's skin where the user wishes to place the sensor. In other embodiments, the sensor insertion assembly may be self-arming, allowing for ease of insertion of the sensor. Examples of such embodiments can be found in, among others, U.S. patent application Ser. No. 12/129,573, now U.S. Pat. No. 8,613,703, the disclosure of which is incorporated herein by reference for all purposes.

Additional embodiments of analyte sensor insertion devices can be found in, among others, U.S. patent application Ser. No. 11/552,072, now U.S. Pat. No. 9,788,771, Ser. No. 13/434,804, now U.S. Pat. No. 9,743,862, Ser. No. 11/216,932, now U.S. Pat. No. 7,731,657, Ser. No. 11/617, 698, now U.S. Pat. No. 8,545,403, Ser. No. 11/380,883, and 11/535,983, now U.S. Pat. No. 7,697,967, the disclosures of which are incorporated herein by reference for all purposes. Such embodiments include insertion devices utilizing variable speed insertion, by varying the speed of the shuttle through the insertion device; shape memory alloy insertion devices, wherein the introducer is constructed of a shape memory alloy that changes shape from a compressed state to a rigid insertion shape upon activation of the shape memory alloy; and coupleable insertion devices and on-skin mounting units, wherein the systems are configured such that the insertion device and on-skin mounting unit can only be coupled in a position such that the insertion device is aligned for proper sensor insertion.

Various other modifications and alterations in the structure and method of operation of this present disclosure will be apparent to those skilled in the art without departing from the scope and spirit of the present disclosure. Although the present disclosure has been described in connection with specific embodiments, it should be understood that the present disclosure as claimed should not be unduly limited to such specific embodiments. It is intended that the following claims define the scope of the present disclosure and that structures and methods within the scope of these claims. Additional detailed description of embodiments of the disclosed subject matter are provided in but not limited to: U.S. Pat. Nos. 7,299,082; 7,167,818; 7,041,468; 6,942,518; 6,893,545; 6,881,551; 6,773,671; 6,764,581; 6,749,740; 6,746,582; 6,736,957; 6,730,200; 6,676,816; 6,618,934; 6,616,819; 6,600,997; 6,592,745; 6,591,125; 6,560,471; 6,540,891; 6,514,718; 6,514,460; 6,503,381; 6,461,496; 6,377,894; 6,338,790; 6,299,757; 6,284,478; 6,270,455; 6,175,752; 6,161,095; 6,144,837; 6,143,164; 6,121,009; 6,120,676; 6,071,391; 5,918,603; 5,899,855; 5,822,715; 5,820,551; 5,628,890; 5,601,435; 5,593,852; 5,509,410; 5,320,715; 5,264,014; 5,262,305; 5,262,035; 4,711,245; 4,545,382; 5,356,786; 5,543,326; 6,103,033; 6,134,461; 6,143,164; 6,144,837; 6,161,095; 6,579,690; 6,605,200; 6,605,201; 6,618,934; 6,654,625; 6,676,816; 6,730,200; 6,736,957; and 6,932,892; and U.S. Publication Nos. 2004/0186365; 2005/0182306; 2006/0025662; 2006/0091006; 2007/0056858; 2007/0068807; 2007/0095661; 2007/0108048; 2007/0199818; 2007/0227911; 2007/0233013; 2008/0066305; 2008/0081977; 2008/0102441; 2008/0148873; 2008/0161666; 2008/0267823; and 2009/0054748; and U.S. patent application Ser. No. 10/745,878, filed Dec. 26, 2003, now U.S. Pat. No. 7,811,231; U.S. patent application Ser. No. 12/143,731, filed Jun. 20, 2008, now U.S. Pat. No. 8,597,188; U.S. patent application Ser. No. 12/143,734, filed Jun. 20, 2008, now U.S. Pat. No. 8,617,069; U.S. Provisional Application No. 61/149,639, filed Feb. 3, 2009; U.S. Provisional Application No. 61/291,326 filed Dec. 30, 2009, and U.S. Provisional Application No. 61/299,924 filed Jan. 29, 2010; U.S. patent application Ser. No. 11/461,725, now U.S. Pat. No. 7,866,026; U.S. patent application Ser. No. 12/131,012; U.S. patent application Ser. No. 12/242,823, now U.S. Pat. No. 8,219,173; U.S. patent application Ser. No. 12/363,712, now U.S. Pat. No. 8,346,335; U.S. patent application Ser. No. 12/698,124; U.S. patent application Ser. No. 12/698,129, now U.S. Pat. No. 9,402,544; U.S. patent application Ser. No. 12/714,439; U.S. patent application Ser. No. 12/794,721, now U.S. Pat. No. 8,595,607; U.S. patent application Ser. No. 12/842,013, now U.S. Pat. No. 9,795,326; U.S. Provisional Application No. 61/238,646; U.S. Provisional Application No. 61/345,562; U.S. Provisional Application No. 61/361,374; and elsewhere, the disclosures of each are incorporated by reference in their entirety herein for all purposes.

The foregoing only illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody the principles of the disclosed subject matter and are thus within the spirit and scope of the disclosed subject matter.

The invention claimed is:

1. A sensor insertion assembly, comprising:
an inserter housing;
an analyte sensor;
a shuttle disposed within the inserter housing, the shuttle coupled to an introducer sharp, a drive spring, and a retraction spring,
  wherein the drive spring, upon release, is configured to displace the shuttle and the introducer sharp in a distal direction and to insert at least a portion of the analyte sensor in fluid contact with a bodily fluid under a skin layer, and
  wherein the retraction spring, upon release, is configured to displace the shuttle and the introducer sharp in a proximal direction;

an actuator mechanism configured to release the drive spring; and a removable safety clip configured to impede actuation of the actuator mechanism, wherein the removable safety clip comprises a first leg portion, a second leg portion, and a bridging portion connecting the first and the second leg portions, and wherein the first and the second leg portions are biased in an inward direction.

2. The sensor insertion assembly of claim 1, further comprising a mounting unit configured to releasably couple with the inserter housing.

3. The sensor insertion assembly of claim 2, wherein the mounting unit includes an aperture through which the introducer sharp and the at least a portion of the analyte sensor are positioned under a skin layer upon release of the drive spring.

4. The sensor insertion assembly of claim 2, wherein the mounting unit includes an adhesive bottom surface.

5. The sensor insertion assembly of claim 2, wherein the mounting unit is configured to receive a sensor electronics unit after the inserter housing is uncoupled from the mounting unit.

6. The sensor insertion assembly of claim 2, wherein the first leg portion includes a first foot portion, wherein the second leg portion includes a second foot portion, and wherein the first and the second foot portions are configured to releasably engage one or more apertures on an exterior surface of the sensor insertion assembly.

7. The sensor insertion assembly of claim 6, wherein the first and the second foot portions are biased in an inward direction.

8. The sensor insertion assembly of claim 6, wherein the first and the second foot portions are configured to disengage from the one or more apertures upon application of one or more forces to the first and the second leg portions.

9. The sensor insertion assembly of claim 8, wherein the one or more forces comprises a squeezing force.

10. The sensor insertion assembly of claim 1, wherein the actuator mechanism comprises at least one depressible button.

11. The sensor insertion assembly of claim 10, wherein the removable safety clip is further configured to prevent the at least one depressible button from being depressed.

12. The sensor insertion assembly of claim 1, wherein the removable safety clip is further configured to disengage from the sensor insertion assembly upon application of one or more forces to the first and the second leg portions.

13. The sensor insertion assembly of claim 1, wherein the at least a portion of the analyte sensor is disposed in a channel of the introducer sharp while the drive spring is in a compressed state.

14. The sensor insertion assembly of claim 1, wherein the drive spring and the retraction spring comprise compression springs.

15. The sensor insertion assembly of claim 1, wherein the drive spring and the retraction spring are each in a compressed state prior to the actuation of the actuator mechanism.

16. The sensor insertion assembly of claim 1, wherein the analyte sensor is a glucose sensor.

17. The sensor insertion assembly of claim 1, wherein the bridging portion comprises a flexible plastic material.

18. The sensor insertion assembly of claim 1, wherein a diameter of the drive spring is greater than a diameter of the retraction spring.

19. The sensor insertion assembly of claim 1, wherein the analyte sensor includes a distal portion and a proximal portion, the distal portion configured to be in fluid contact with subcutaneous bodily fluid and having a width smaller than a width of the proximal portion.

20. A sensor insertion assembly, comprising:

an inserter housing;

an analyte sensor;

a mounting unit configured to releasably couple with the inserter housing;

a shuttle disposed within the inserter housing, the shuttle coupled to an introducer sharp, a drive spring, and a retraction spring, wherein the drive spring, upon release, is configured to displace the shuttle and the introducer sharp in a distal direction and to insert at least a portion of the analyte sensor in fluid contact with a bodily fluid under a skin layer, and wherein the retraction spring, upon release, is configured to displace the shuttle and the introducer sharp in a proximal direction;

an actuator mechanism configured to release the drive spring; and a removable safety clip configured to impede actuation of the actuator mechanism, wherein the removable safety clip comprises a first leg portion, a second leg portion, and a bridging portion connecting the first and the second leg portions, and wherein the first leg portion includes a first foot portion, wherein the second leg portion includes a second foot portion, and wherein the first and the second foot portions are configured to releasably engage one or more apertures on an exterior surface of the sensor insertion assembly.

21. The sensor insertion assembly of claim 20, wherein the first and the second leg portions are biased in an inward direction.

22. The sensor insertion assembly of claim 20, wherein the mounting unit includes an adhesive bottom surface.

23. The sensor insertion assembly of claim 20, wherein the mounting unit is configured to receive a sensor electronics unit after the inserter housing is uncoupled from the mounting unit.

24. The sensor insertion assembly of claim 20, wherein the first and the second foot portions are biased in an inward direction.

25. The sensor insertion assembly of claim 20, wherein the actuator mechanism comprises at least one depressible button.

26. The sensor insertion assembly of claim 25, wherein the removable safety clip is further configured to prevent the at least one depressible button from being depressed.

27. The sensor insertion assembly of claim 20, wherein the removable safety clip is configured to disengage from the sensor insertion assembly upon application of one or more forces to the first and the second leg portions.

28. The sensor insertion assembly of claim 20, wherein the first and the second foot portions are configured to disengage from the one or more apertures upon application of one or more forces to the first and the second leg portions.

29. The sensor insertion assembly of claim 20, wherein the one or more forces comprises a squeezing force.

30. The sensor insertion assembly of claim 20, wherein the at least a portion of the analyte sensor is disposed in a channel of the introducer sharp while the drive spring is in a compressed state.

31. The sensor insertion assembly of claim 20, wherein the drive spring and the retraction spring comprise compression springs.

32. The sensor insertion assembly of claim 20, wherein the drive spring and the retraction spring are each in a compressed state prior to the actuation of the actuator mechanism.

33. The sensor insertion assembly of claim 20, wherein the analyte sensor is a glucose sensor.

34. The sensor insertion assembly of claim 20, wherein the mounting unit includes an aperture through which the introducer sharp and the at least portion of the analyte sensor are positioned under a skin layer upon release of the drive spring.

35. The sensor insertion assembly of claim 20, wherein the bridging portion comprises a flexible plastic material.

36. The sensor insertion assembly of claim 20, wherein a diameter of the drive spring is greater than a diameter of the retraction spring.

37. The sensor insertion assembly of claim 20, wherein the analyte sensor includes a distal portion and a proximal portion, the distal portion configured to be in fluid contact with subcutaneous bodily fluid and having a width smaller than a width of the proximal portion.

* * * * *